(12) United States Patent
Deriso

(10) Patent No.: US 11,064,950 B2
(45) Date of Patent: Jul. 20, 2021

(54) HAND-HELD HEART MONITORING DEVICE

(71) Applicant: Simple Health Labs, Inc., San Francisco, CA (US)

(72) Inventor: David Michael Deriso, San Francisco, CA (US)

(73) Assignee: Bluue Co., San Francisco, CA (US)

( * ) Notice: Subject to any disclaimer, the term of this patent is extended or adjusted under 35 U.S.C. 154(b) by 79 days.

(21) Appl. No.: 16/173,874

(22) Filed: Oct. 29, 2018

(65) Prior Publication Data

US 2019/0125270 A1 May 2, 2019

Related U.S. Application Data

(60) Provisional application No. 62/682,180, filed on Jun. 8, 2018, provisional application No. 62/578,274, filed on Oct. 27, 2017.

(51) Int. Cl.
| | |
|---|---|
| *A61B 5/00* | (2006.01) |
| *A61B 5/1455* | (2006.01) |
| *A61B 7/04* | (2006.01) |
| *A61B 8/06* | (2006.01) |
| *A61B 8/08* | (2006.01) |
| *A61B 5/0205* | (2006.01) |
| *A61B 5/282* | (2021.01) |
| *A61B 5/332* | (2021.01) |

(52) U.S. Cl.
CPC .......... *A61B 5/7221* (2013.01); *A61B 5/0205* (2013.01); *A61B 5/14551* (2013.01);
(Continued)

(58) Field of Classification Search
USPC .......................................... 600/513
See application file for complete search history.

(56) References Cited

U.S. PATENT DOCUMENTS

| | | |
|---|---|---|
| 2001/0000526 A1 | 4/2001 | Gopinathan et al. |
| 2006/0139331 A1 | 6/2006 | Olson |
| (Continued) | | |

FOREIGN PATENT DOCUMENTS

| | | |
|---|---|---|
| CN | 1923136 A | 3/2007 |
| KR | 101042827 B1 | 6/2011 |
| (Continued) | | |

OTHER PUBLICATIONS

McCombie, D.B. et al, "Adaptive blood pressure estimation from wearable PPG sensors using peripheral artery pulse wave velocity measurements and multi-channel blind identification of local arterial dynamics," 28th International Conference of the IEEE in Engineering in Medicine and Biology Society, 2006, pp. 3521-3524.
(Continued)

*Primary Examiner* — Nicole F Lavert
*Assistant Examiner* — Nicole F Johnson
(74) *Attorney, Agent, or Firm* — Fenwick & West LLP

(57) ABSTRACT

A heart monitoring device comprises an enclosure with various sensors and components. The enclosure has a first groove on a top surface, sized to fit a phalange of a subject's right hand. When the device is held with the corresponding phalange keyed into the first groove, the device is in a proper orientation for recording the subject's heart activity. The device includes a plurality of electrodes configured to create one or more electrical circuits across a human heart. The electrodes include a right thumb electrode placed on a side of the enclosure for coupling to the subject's right thumb and an upper chest electrode and a lower chest electrode placed on a bottom surface of the enclosure for coupling to the subject's chest. The heart monitoring device also has a plurality of pulse oximeters placed in the first groove and configured to measure blood oxygen levels of the corresponding phalange.

21 Claims, 21 Drawing Sheets

(52) U.S. Cl.
CPC .............. *A61B 5/282* (2021.01); *A61B 5/332* (2021.01); *A61B 5/6823* (2013.01); *A61B 5/6826* (2013.01); *A61B 7/04* (2013.01); *A61B 8/06* (2013.01); *A61B 8/488* (2013.01); *A61B 5/0006* (2013.01); *A61B 5/6843* (2013.01); *A61B 5/721* (2013.01); *A61B 2560/0425* (2013.01); *A61B 2562/0204* (2013.01); *A61B 2562/0214* (2013.01); *A61B 2562/0215* (2017.08); *A61B 2562/0219* (2013.01); *A61B 2562/0252* (2013.01)

(56) References Cited

U.S. PATENT DOCUMENTS

| | | |
|---|---|---|
| 2010/0042008 A1 | 2/2010 | Amitai et al. |
| 2011/0063219 A1 | 3/2011 | Min-Liang et al. |
| 2014/0114166 A1 | 4/2014 | Baxi |
| 2014/0135631 A1* | 5/2014 | Brumback ............... A61B 5/11 600/479 |
| 2015/0272466 A1 | 10/2015 | Laakkonen et al. |
| 2016/0235325 A1 | 8/2016 | Chou |

FOREIGN PATENT DOCUMENTS

| | | |
|---|---|---|
| WO | WO 2017/053847 A1 | 3/2017 |
| WO | WO 2017/173434 A1 | 10/2017 |

OTHER PUBLICATIONS

PCT International Search Report and Written Opinion, PCT Application No. PCT/US18/58021, dated Dec. 28, 2018, 21 pages.

* cited by examiner

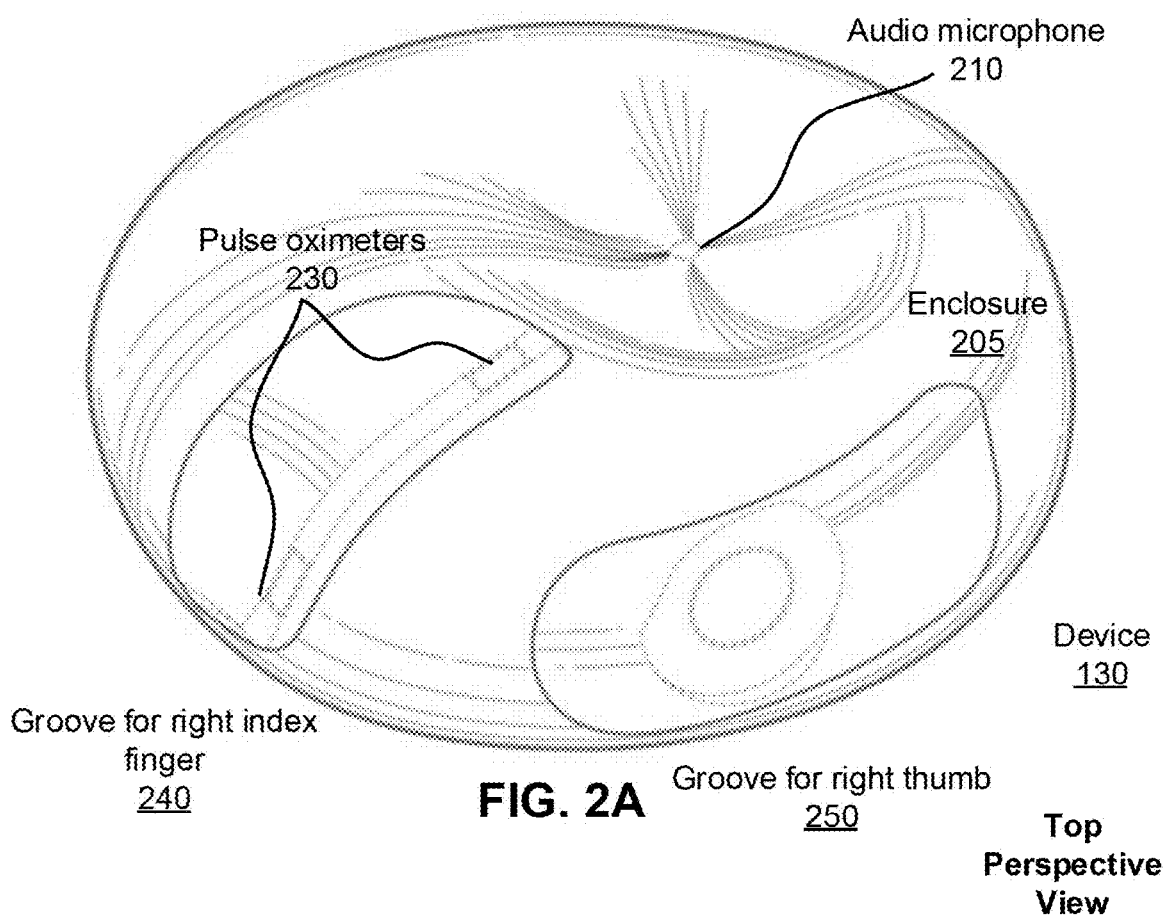
FIG. 2A Top Perspective View
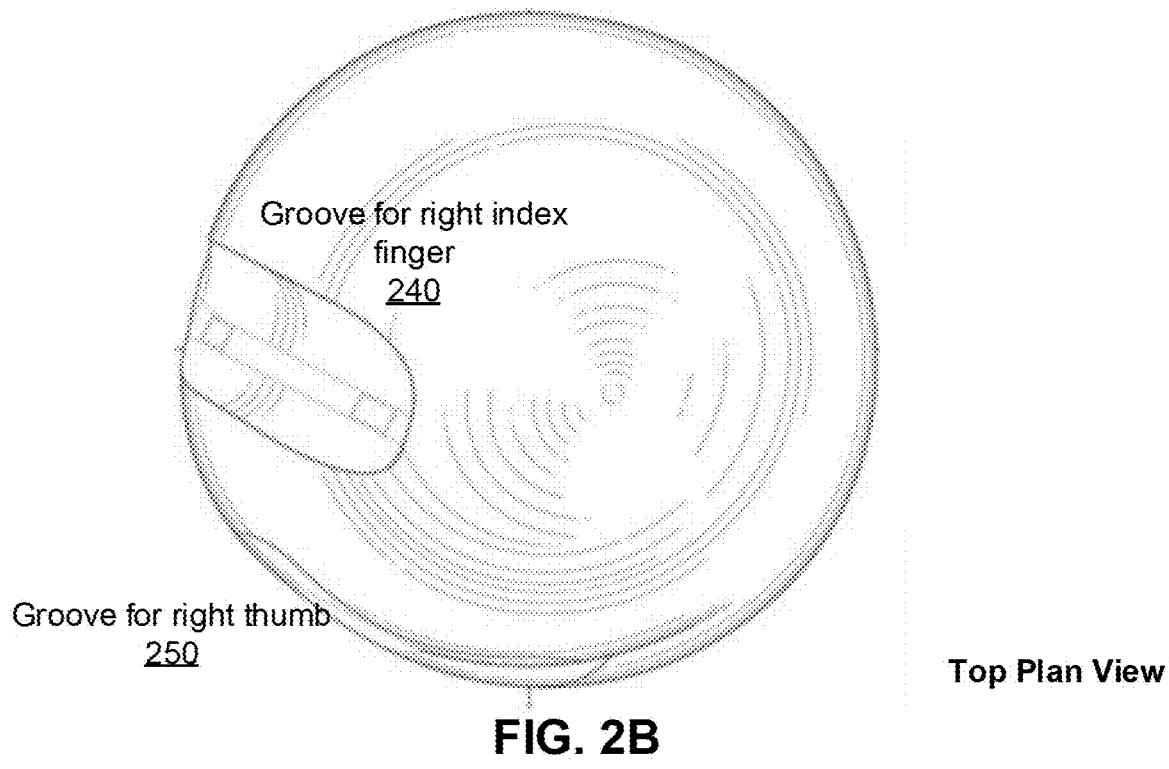
FIG. 2B Top Plan View

HAND-HELD HEART MONITORING DEVICE

CROSS REFERENCE TO RELATED APPLICATIONS

This application claims the benefit of U.S. Provisional Application No. 62/578,274, filed Oct. 27, 2017, and U.S. Provisional Application No. 62/682,180, filed Jun. 8, 2018, which are incorporated by reference in their entirety.

BACKGROUND

This disclosure relates generally to a heart monitoring device for recording heart data of a subject of the heart monitoring device.

Specifically, heart monitors may include electrocardiogram (EKG or ECG) monitors which utilize electrodes to measure electrical activity across the heart of a subject. The goal of EKG monitors is to provide a comprehensive record of a subject's heart activity as measured by the electrodes. This goal is generally achieved through maximizing signal quality of data channels, reducing recording artifacts, and improving ease of use of the EKG monitors. Current hand-held EKG monitors either lack in measuring sufficient heart data (e.g., a one-dimensional (1D) measurement of a heart's electrical activity or only measuring one type of heart activity), in ease of application of the monitors (e.g., monitors that take many steps prior to recording), in ease of recording heart activity, or some combination thereof. These disadvantages may also lead to user discomfort and poor user experience.

SUMMARY

Described herein is an accurate, precise, and easy-to-use heart monitoring device (referred to as the "device").

In one embodiment, the heart monitoring device is a hand-held monitor which when held against a chest of a subject by a subject's right hand in a restricted orientation is capable of recording heart activity. To restrict the orientation, the heart monitoring device has topographical features that key to a subject's right hand such that, when the heart monitoring device is held in the subject's right hand against the subject's chest, there is a limited range of orientations that the heart monitoring device can be in. The heart monitoring device includes at least three electrodes for measuring heart electrical activity with one coupled to a subject's right hand thumb and two coupled to a subject's chest when the heart monitoring device is held in a proper orientation. When held against a subject's chest, the heart monitoring device is able to provide a two-dimensional (2D) reading of the subject's heart electrical activity by completing two electrical circuits across the heart. In addition, the heart monitoring device includes pulse oximeters that are placed at a fixed distance and configured to measure blood oxygen levels at a subject's finger which can be used to calculate blood pressure, among other characteristics of the subject's heart. Due to the placement of the two pulse oximeters, the heart monitoring device is able to precisely calculate measurements of a pulse wave velocity of the subject in light of knowing the fixed distance between the two pulse oximeters. The precision in measuring the pulse wave velocity also provides more precise calculations of a blood pressure of the subject. The combination of measuring both blood pressure and heart electrical activity with a single device over a single time period greatly improves the efficiency in measuring both characteristics of a subject's heart. In other embodiments, the heart monitoring device also includes any combination of other sensors such as audio microphones, a Doppler sensor, a force sensor, a reed switch, and movement sensors.

Methods for accurately measuring a target subject's heart activity using the heart monitoring device are also disclosed herein. In one embodiment, a method may include various combination of prompting of the target subject and monitoring with sensors on the heart monitoring device. The heart monitoring device may use this method for determining whether a recording session produces a valid recording or an invalid recording of the target subject's heart activity.

In one embodiment, the heart monitoring device comprises an enclosure sized to fit a subject's right hand with a top surface for coupling to the subject's right hand and a bottom surface for coupling to the subject's chest, the enclosure comprising a first groove on the top surface and sized to fit a corresponding phalange of the subject's right hand, wherein the heart monitoring device has a proper orientation for recording heart activity of the subject, the proper orientation comprising a range of orientations of the heart monitoring device relative to the subject when the heart monitoring device is held by the subject with the corresponding phalange keyed into the first groove; a plurality of electrodes placed on the enclosure and configured to create one or more electrical circuits across a human heart when the heart monitoring device is in the proper orientation, the plurality of electrodes including; a right thumb electrode placed on a side surface of the enclosure for coupling to the subject's right thumb, and an upper chest electrode and a lower chest electrode placed on the bottom surface of the enclosure for coupling to the subject's chest; and a plurality of pulse oximeters placed in the first groove and configured to measure blood oxygen levels of the corresponding phalange when the corresponding phalange is keyed into the first groove.

In one embodiment of the heart monitoring device, the enclosure comprises a second groove on the side surface of the enclosure and sized to fit a subject's right thumb, wherein the right thumb electrode is placed in the second groove.

In one embodiment of the heart monitoring device, the plurality of electrodes are dry contact electrodes comprises a conductive surface with topographical features, the conductive surface for coupling to the subject's chest.

In one embodiment of the heart monitoring device, the conductive surface of each electrode is constructed with silver.

In one embodiment of the heart monitoring device, the electrical circuits created by the plurality of electrodes includes a first electrical circuit that is completed with the right thumb electrode and the upper chest electrode which is used by the heart monitoring device to define a first lead across the subject's heart; and a second electrical circuit that is completed with the right thumb electrode and the lower chest electrode which is used by the heart monitoring device to define a second lead across the subject's heart.

In one embodiment of the heart monitoring device, the first lead and the second lead are noncollinear based at least in part on the proper orientation of the heart monitoring device relative to the subject.

In one embodiment of the heart monitoring device, a third lead is calculated based at least in part on a basis formed by the first lead and the second lead.

In one embodiment of the heart monitoring device, the heart monitoring device further comprises a first audio microphone placed within the enclosure and configured to record acoustic signals from a local area of the heart monitoring device.

In one embodiment of the heart monitoring device, the heart monitoring device further comprises a second audio microphone placed within the enclosure in proximity to the bottom surface of the enclosure and configured to record acoustic signals from the subject's chest.

In one embodiment of the heart monitoring device, the heart monitoring device further comprises a Doppler sensor placed on the bottom surface of the enclosure and configured to record a Doppler shift signal corresponding to flow of blood in the subject.

In one embodiment of the heart monitoring device, the heart monitoring device further comprises a force sensor placed within the enclosure and coupled to one of the upper chest electrode and the lower chest electrode, wherein the force sensor is configured to measure a force applied onto the electrode to which the force sensor is coupled.

In one embodiment of the heart monitoring device, the heart monitoring device further comprises a movement sensor placed within the enclosure and configured to measure movement of the heart monitoring device.

In one embodiment of the heart monitoring device, the heart monitoring device comprises an enclosure sized to fit a subject's hand with a top surface for coupling to the subject's hand and a bottom surface for coupling to the subject's chest; a plurality of electrodes placed on the enclosure and configured to create one or more electrical circuits across a human heart when the heart monitoring device is held in the subject's hand against the subject's chest, the plurality of electrodes including a thumb electrode placed on a side surface of the enclosure for coupling to a thumb of the subject's hand, and one or more chest electrodes placed on the bottom surface of the enclosure for coupling to the subject's chest.

In one embodiment of the method for accurately recording heart activity of a target subject with the heart monitoring device, the method comprises prompting the target subject to hold the heart monitoring device in a proper orientation, wherein the proper orientation occurs when the subject's right hand holds the heart monitoring device against the subject's chest, such that a corresponding phalange on the subject's right hand keys into a first groove on a top surface of an enclosure of the heart monitoring device; prompting the target subject to state a phrase while holding the heart monitoring device; receiving a first acoustic signal from a first audio microphone placed within the enclosure in proximity to a bottom surface of the enclosure and configured to record acoustic signals from the subject's chest; determining whether the target subject is holding the heart monitoring device against the target subject's chest based at least in part on the first acoustic signal; activating one or more sensors of the heart monitoring device to measure heart data; receiving the heart data from the sensors from a recording session; determining presence of or lack of one or more recording artifacts during the recording session based at least in part on the heart data; and responsive to determining a lack of recording artifacts during the recording session, determining the recording session to be a valid recording.

In one embodiment of the method for accurately recording heart activity of a target subject with the heart monitoring device, the determining whether the target subject is holding the heart monitoring device against the target subject's chest based at least in part on the first acoustic signal comprises determining that the first acoustic signal is above a threshold intensity, wherein the determining whether the target subject is holding the heart monitoring device against the target subject's chest is based on the determining that the first acoustic signal is above a threshold intensity.

In one embodiment of the method for accurately recording heart activity of a target subject with the heart monitoring device, the method further comprises receiving a second acoustic signal from a second audio microphone placed within the enclosure in proximity to the top surface of the enclosure and configured to record acoustic signals from a local area of the heart monitoring device.

In one embodiment of the method for accurately recording heart activity of a target subject with the heart monitoring device, the determining whether the target subject is holding the heart monitoring device against the target subject's chest is also based at least in part on the second acoustic signal comprises determining that the second acoustic signal matches a ground truth acoustic signal of the target subject's voice.

In one embodiment of the method for accurately recording heart activity of a target subject with the heart monitoring device, the determining whether the target subject is holding the heart monitoring device against the target subject's chest is based at least in part on the first acoustic signal and the second acoustic signal comprises determining a synchronicity between the first acoustic signal and the second acoustic signal, wherein the determining whether the target subject is holding the heart monitoring device against the target subject's chest is also based on the synchronicity.

In one embodiment of the method for accurately recording heart activity of a target subject with the heart monitoring device, the sensors include a plurality of electrodes completing one or more electrical circuits across the target subject's heart, and wherein the heart data comprises EKG data including one or more leads measured by the plurality of electrodes with the completed electrical circuits.

In one embodiment of the method for accurately recording heart activity of a target subject with the heart monitoring device, the determining presence of or lack of one or more recording artifacts during the recording session based at least in part on the heart data comprises calculating a noise signal from the EKG data; and determining whether the noise signal surpasses a threshold noise signal, wherein the determination that the noise signal surpasses the threshold noise signal corresponds to determining a presence of one or more recording artifacts, and wherein the determination that the noise signal is below the threshold noise signal corresponds to determining a lack of one or more recording artifacts.

In one embodiment, a system comprises a processor; and a non-transitory computer-readable storage medium with encoded instructions that, when executed by the processor, cause the processor to accomplish steps of: prompting the target subject to hold the heart monitoring device in a proper orientation, wherein the proper orientation occurs when the subject's right hand holds the heart monitoring device against the subject's chest, such that a corresponding phalange on the subject's right hand keys into a first groove on a top surface of an enclosure of the heart monitoring device; prompting the target subject to state a phrase while holding the heart monitoring device; receiving a first acoustic signal from a first audio microphone placed within the enclosure in proximity to a bottom surface of the enclosure and configured to record acoustic signals from the subject's chest; determining whether the target subject is holding the heart monitoring device against the target subject's chest based at least in part on the first acoustic signal; activating one or more sensors of the heart monitoring device to measure heart data; receiving the heart data from the sensors from a recording session; determining presence of or lack of one or more recording artifacts during the recording session based at least in part on the heart data; and responsive to determining a lack of recording artifacts during the recording session, determining the recording session to be a valid recording.

BRIEF DESCRIPTION OF THE DRAWINGS

FIG. 2A illustrates a top perspective view of a heart monitoring device, according to an embodiment.

FIG. 2B illustrates a top plan view of the heart monitoring device, according to an embodiment.

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

I. Overview

Figure 2C:
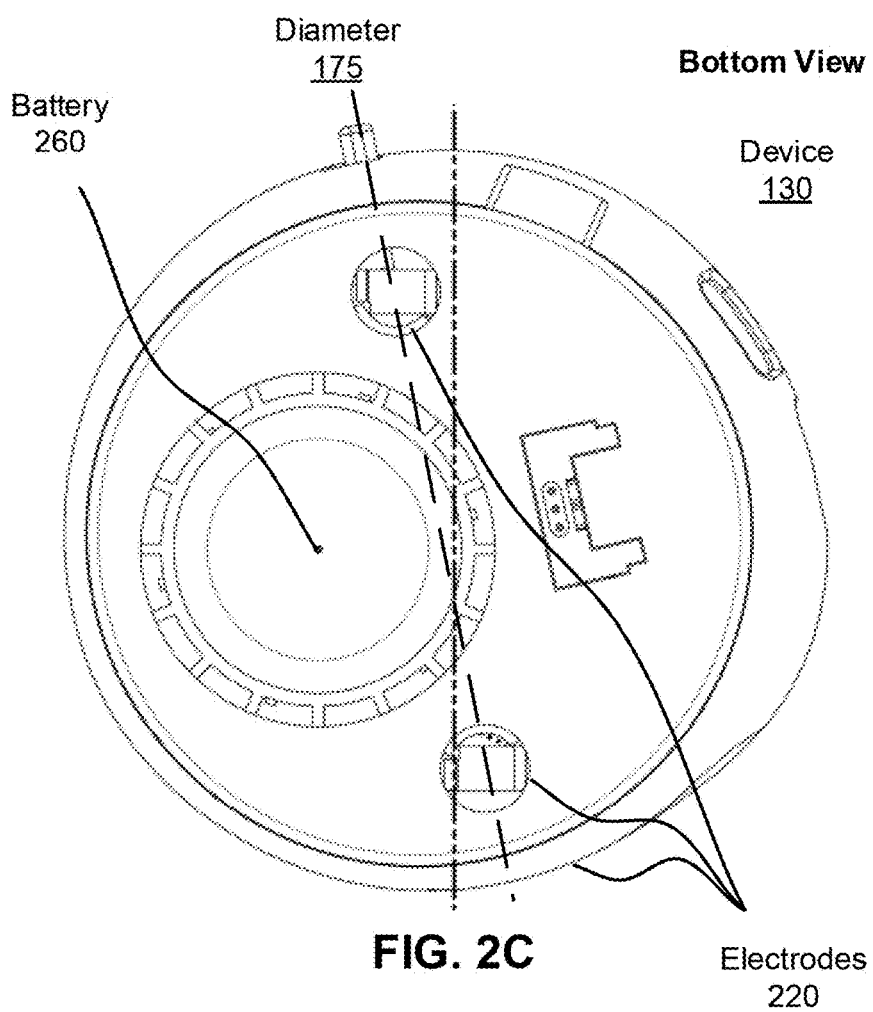
FIG. 2C illustrates a bottom plan view of the heart monitoring device, according to an embodiment.
Figure 2D:
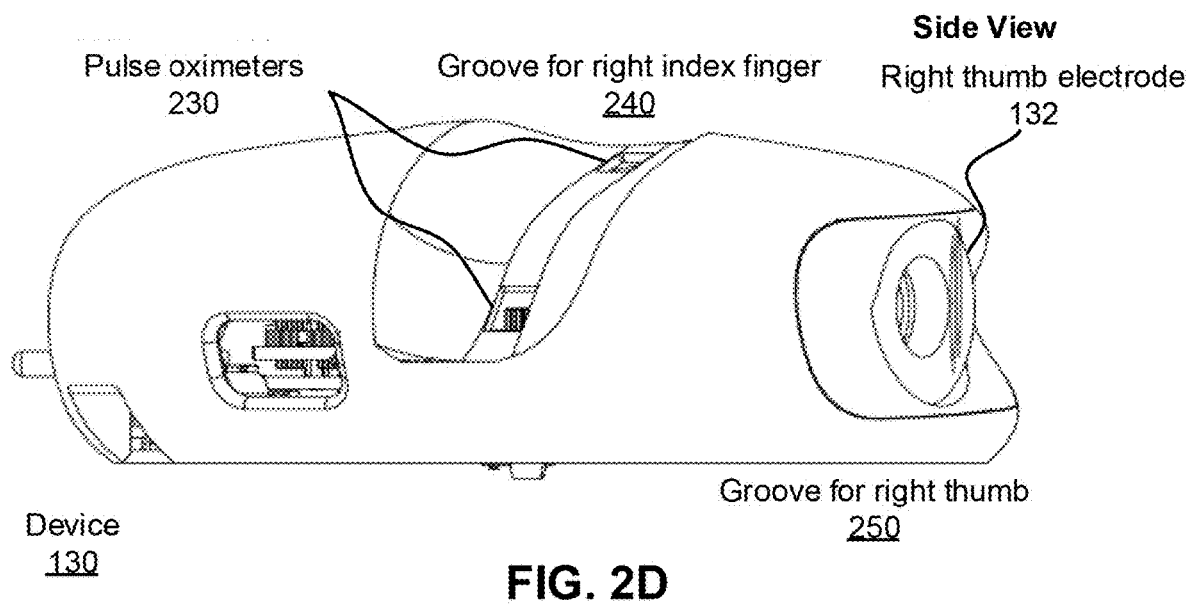
FIG. 2D illustrates a side view of the heart monitoring device, according to an embodiment.
Figure 2E:
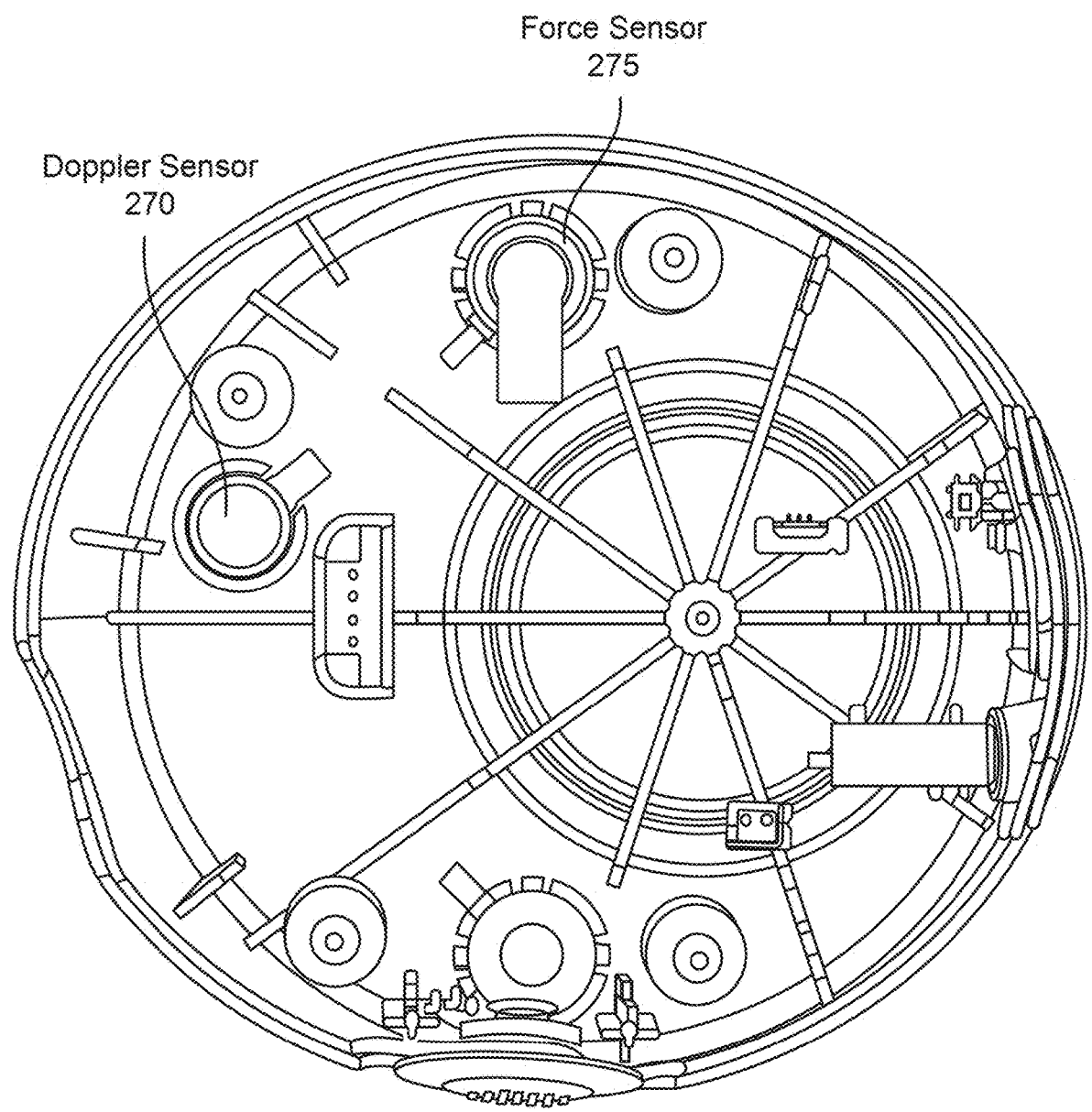
FIG. 2E illustrates a cutaway view of the heart monitoring device from a top plan perspective, according to an embodiment.
Figure 2F:
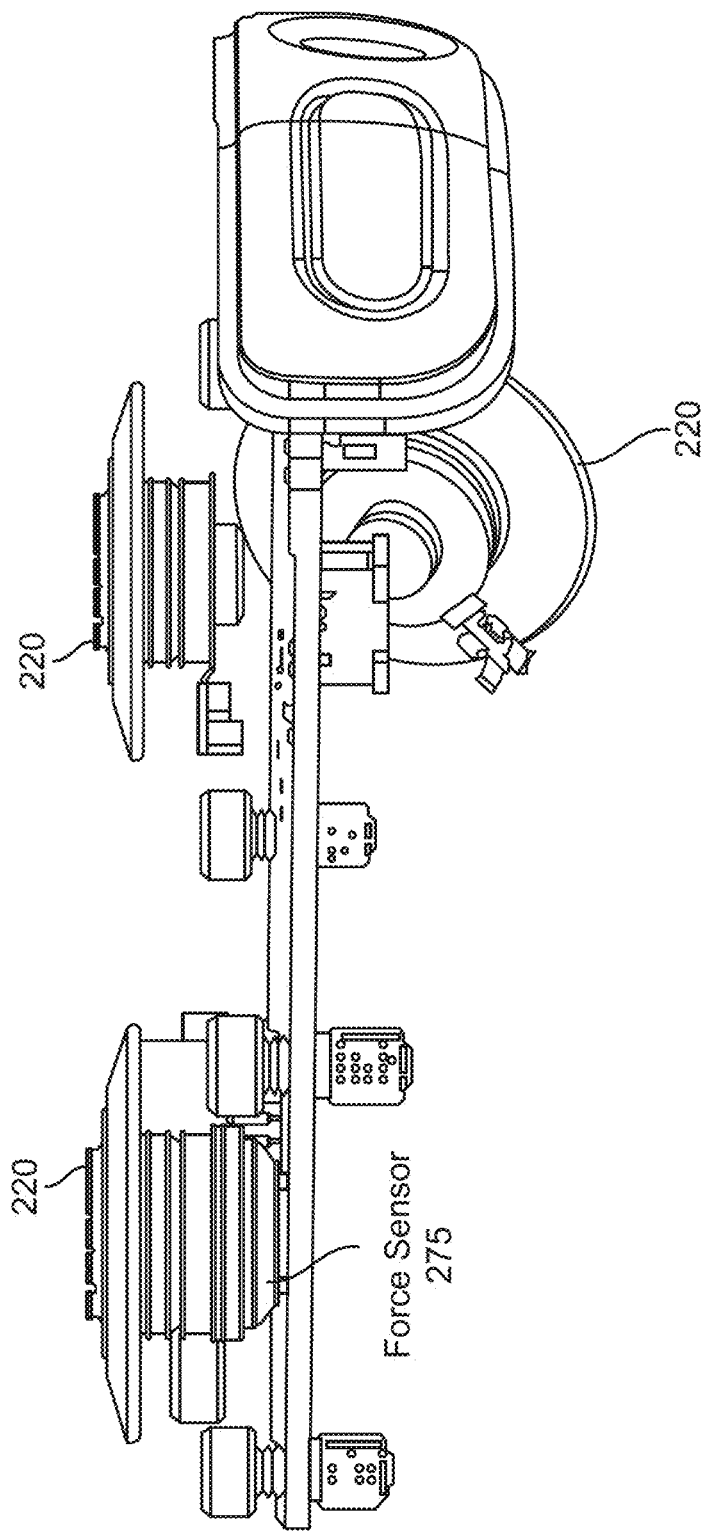
FIG. 2F illustrates a cross sectional view of a portion of the heart monitoring device, according to an embodiment.
Figure 2G:
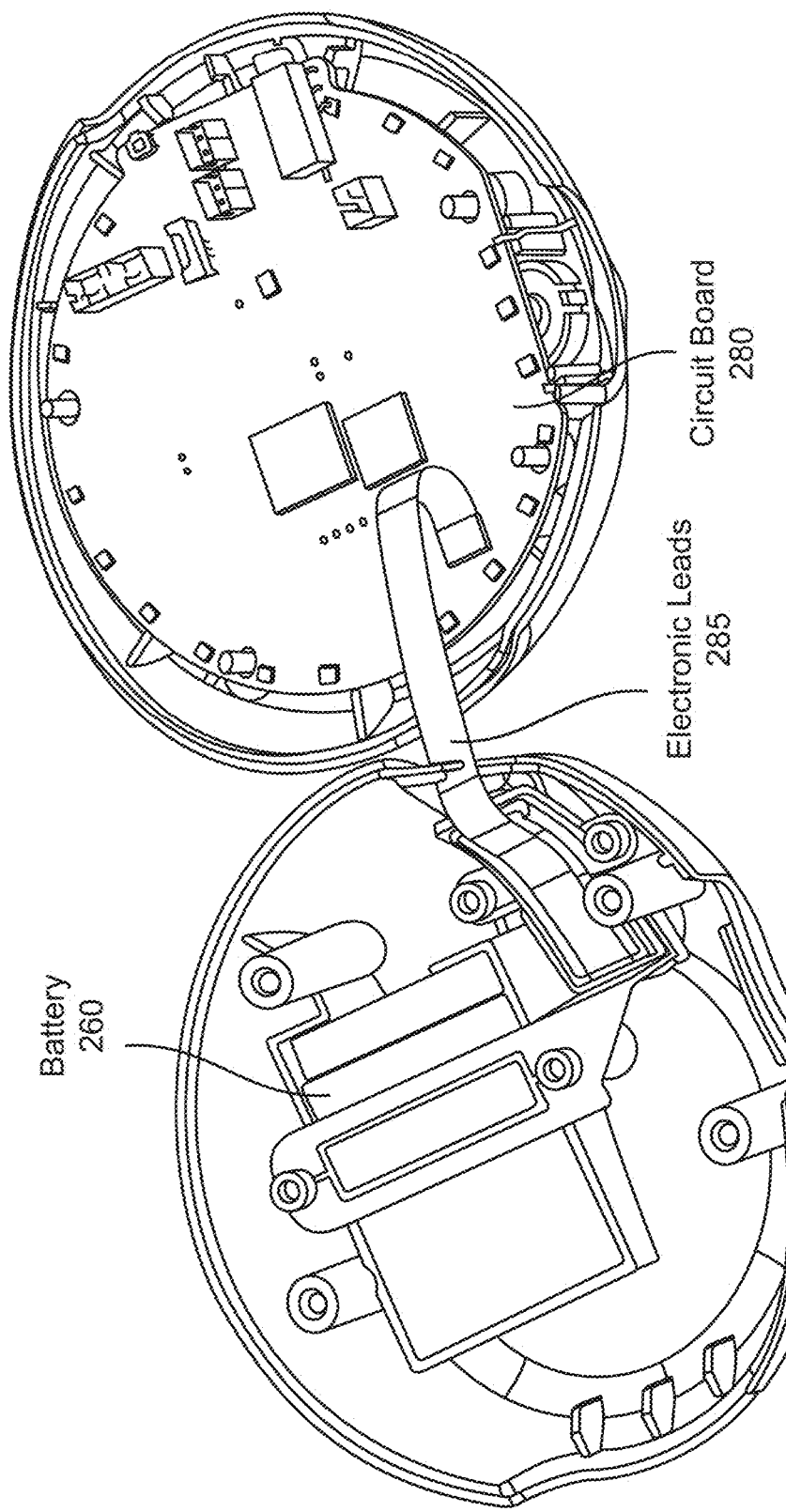
FIG. 2G illustrates an opened configuration of the heart monitoring device, according to an embodiment.
Figure 2H:
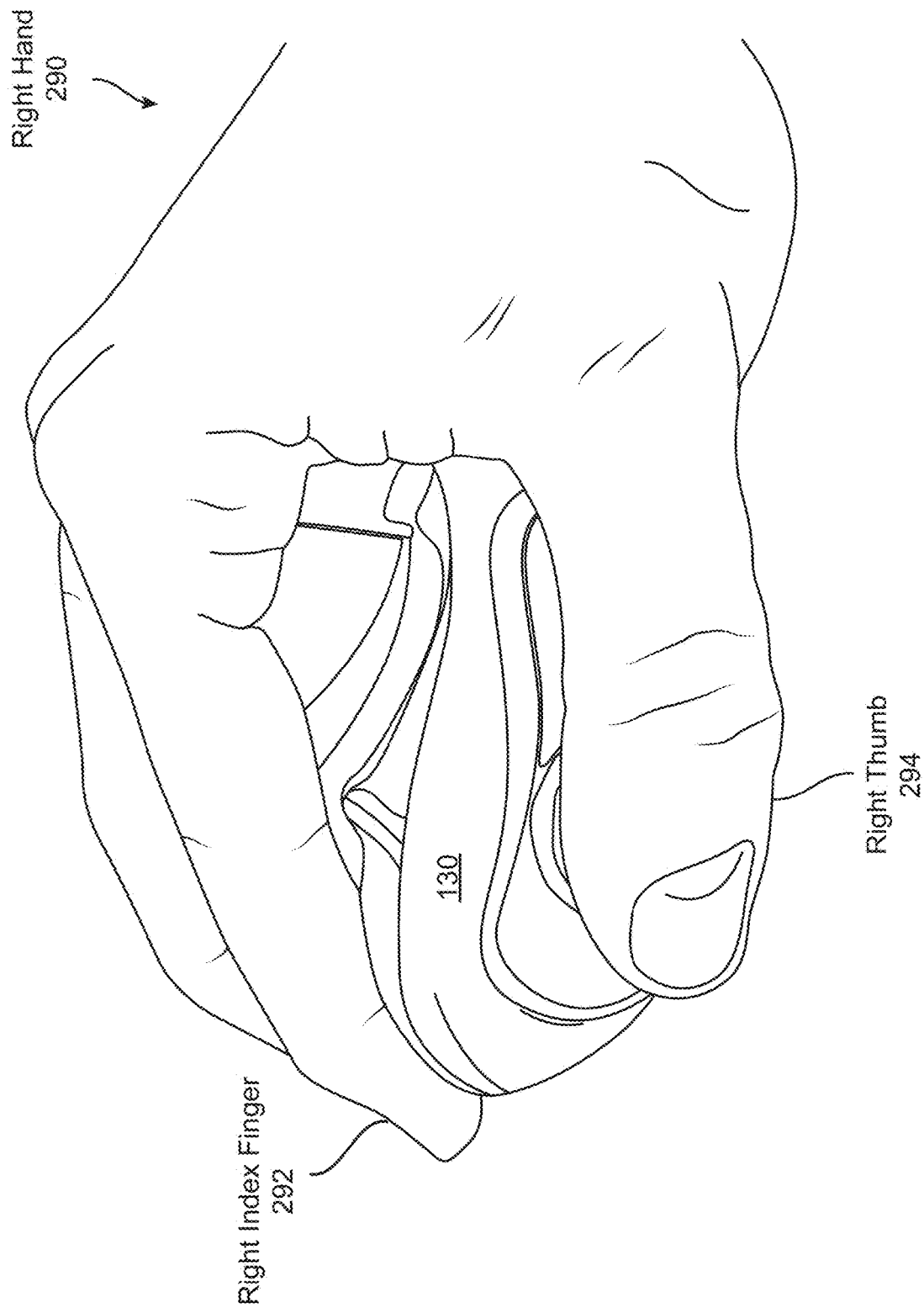
FIG. 2H illustrates the heart monitoring device in relation to a subject's hand, according to an embodiment.

Described herein is an accurate, precise, and easy-to-use heart monitoring device (referred to as the "device"). The heart monitoring device is a hand-held monitor which when held against a chest of a subject by a subject's right hand in a restricted orientation shown in FIGS. 2H, 3D, and 3E, is capable of recording heart activity. In order to restrict an orientation of the heart monitoring device when held against the subject's chest by the subject's right hand, the heart monitoring device has topographical features that aid in restricting the orientation of the heart monitoring device when held. The topographical features include at least one groove in where a finger of the subject rests.

The heart monitoring device includes at least three electrodes for measuring heart electrical activity with one coupled to a subject's right hand thumb and two coupled to a subject's chest when the heart monitoring device is held in a proper orientation. When in the proper orientation, the heart monitoring device is able to provide a two-dimensional (2D) reading of the subject's heart electrical activity by completing two electrical circuits across the heart: a first electrical circuit is completed with a first chest electrode and the right thumb electrode and a second electrical circuit is completed with a second chest electrode and the right thumb electrode. This placement of electrodes is referred to as a reduced two-lead configuration. Two leads or electric potential vectors are measured, one from the first electrical circuit and one from the second electrical circuit. The heart monitoring device may calculate a third potential vector according to Kirchhoff's Law with the two measured electric potential vectors. The two or more electric potential vectors provide the 2D reading of the subject's heart electrical activity which consequently provides better comprehension of the heart's electrical activity compared to a 1D reading from a single electrical circuit (formed with only two electrodes). A 1D reading from a single electrical circuit sets a limitation to accuracy and precision, as the electrical activity of a heart is three-dimensional (3D). Furthermore, a linear combination of a basis formed by two electrical circuits can provide an entire mapping of the heart's electrical activity; whereas, a single dimension measurement cannot.

In addition, the heart monitoring device includes pulse oximeters that are placed at a fixed distance and configured to measure blood oxygen levels at a subject's finger which can be used to calculate blood pressure, among other characteristics of the subject's heart. Due to the placement of the two pulse oximeters, the heart monitoring device is able to precisely calculate measurements of a pulse wave velocity of the subject in light of knowing the fixed distance between the two pulse oximeters. The precision in measuring the pulse wave velocity also provides more precise calculations of a blood pressure of the subject. The combination of measuring both blood pressure and heart electrical activity with a single device over a single time period greatly improves the efficiency in measuring both characteristics of a subject's heart. In other embodiments, the heart monitoring device also includes any combination of one or more microphones, a Doppler sensor, a force sensor, a reed switch, and other sensors.

Methods for accurately measuring a target subject's heart activity using the heart monitoring device are also disclosed herein. The methods may include various combination of prompting of the target subject and monitoring with sensors on the heart monitoring device. The heart monitoring device uses these methods for determining whether a recording session produces a valid recording or an invalid recording of the target subject's heart activity.

II. Example Computing Environment

Figure 1A:
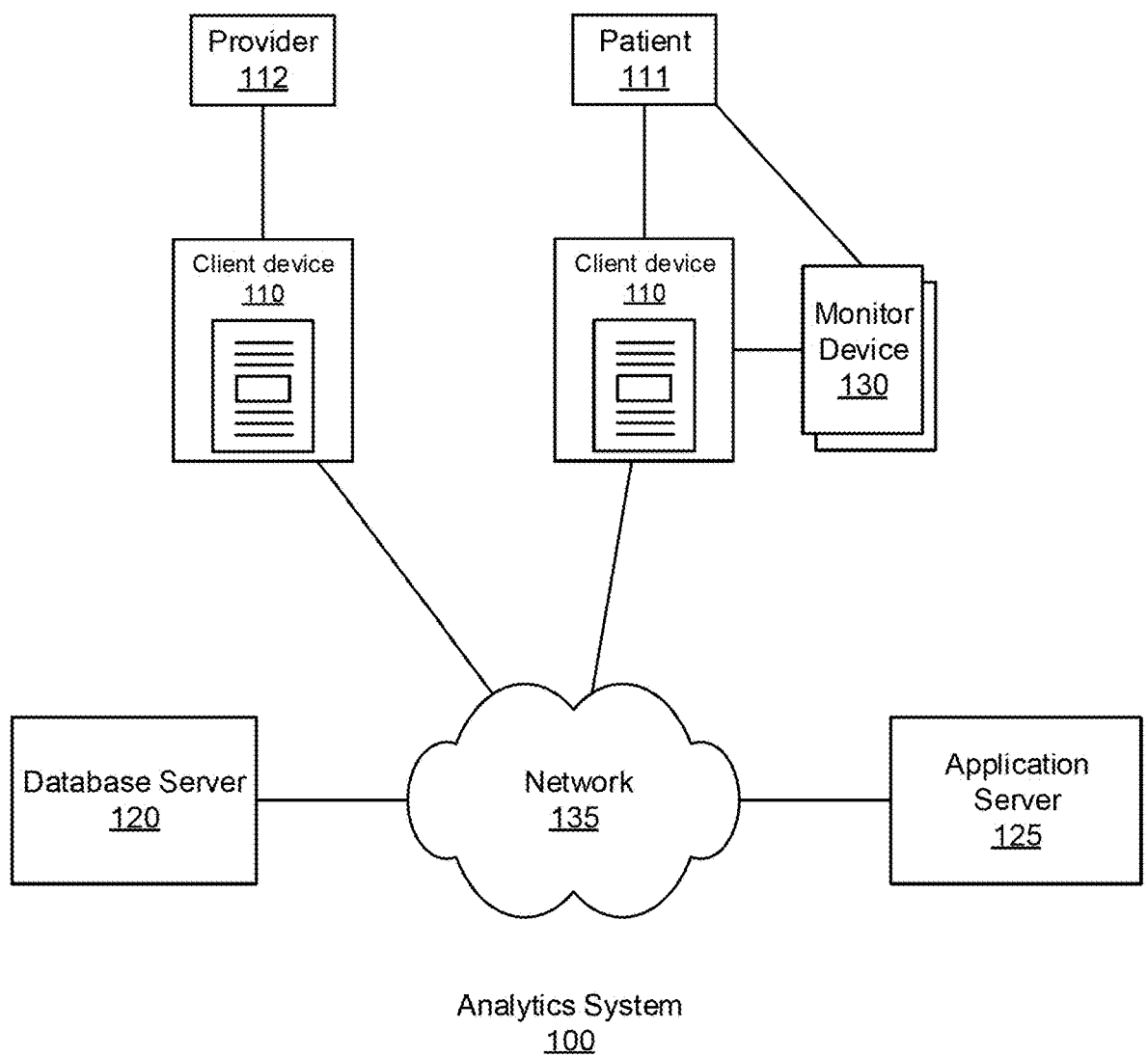
FIG. 1A illustrates an analytics system environment, according to an embodiment.

FIG. 1A shows an analytics system 100 for monitoring accurate, real-time heart activity measurements, performing analytics on that data, and providing summary analytics, according to one embodiment.

The analytics system includes client computing devices 110, a heart monitoring device 130, an application server 125, database server 120, and a network 135. Although FIG. 1A illustrates only a single instance of most of the components of the analytics system 100, in practice more than one of each component may be present, and additional or fewer components may be used.

The client device 110 is a computer system. An example physical implementation is described more completely below with respect to FIG. 1B. The client device 110 is configured to wirelessly communicate with the analytics system 100 via network 135. With network 135 access, the client device 110 transmits to system 100 the subject's measurement data associated with the heart monitoring device 130.

The heart monitoring device 130 includes its own network adapter (not shown) that communicates with the client device 110 either through a wired connection, or more typically through a wireless radio frequency connection. In one embodiment, the network adapter is a Bluetooth Low Energy (BTLE) wireless transmitter, however in other embodiments other types of wireless communication may be used (e.g., infrared, 102.11). In one embodiment, the heart monitoring device 130 is the heart monitoring device 130 for measuring heart activity as described previously in FIGS. 1-4.

Figure 1B:
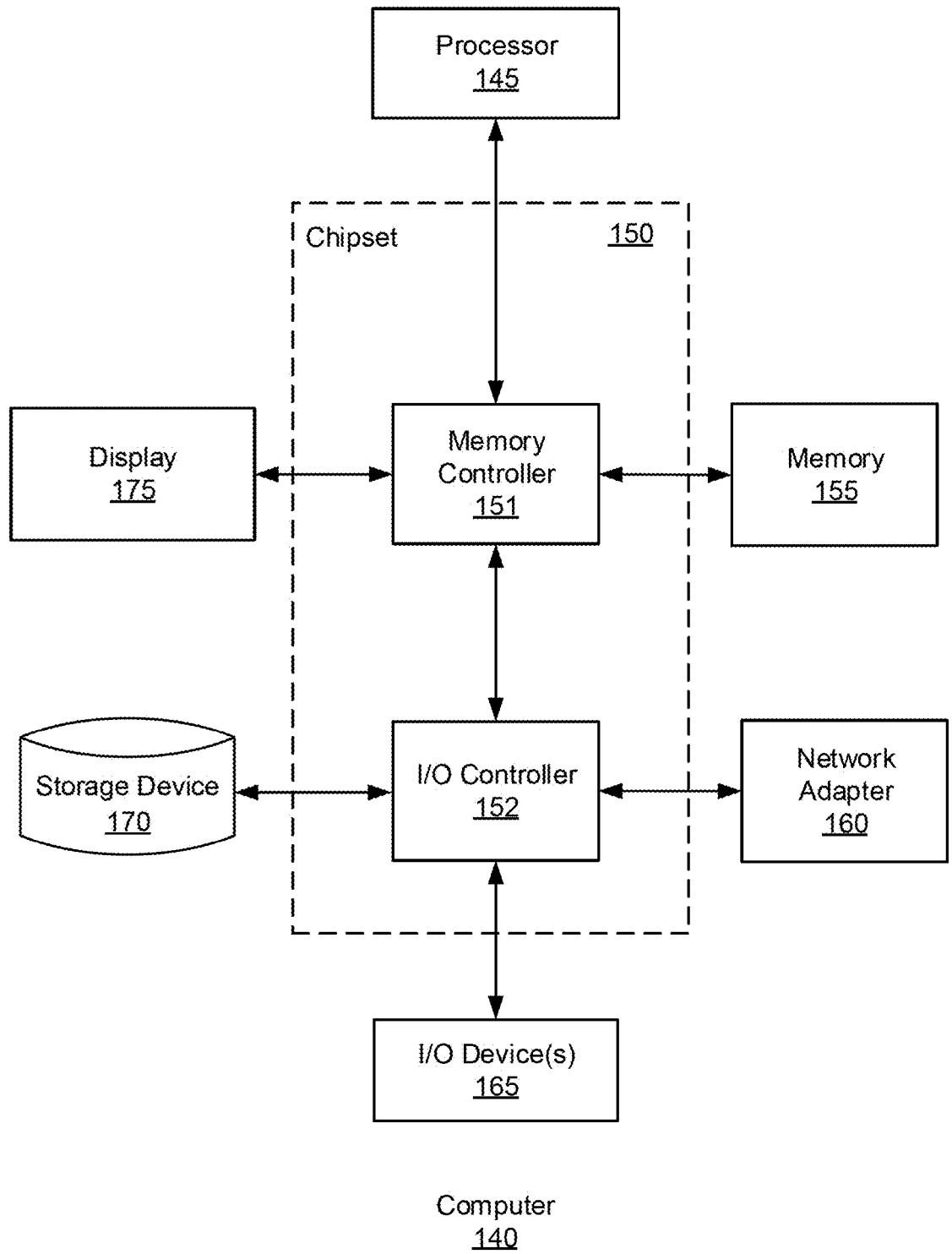
FIG. 1B illustrates an example computer, according to an embodiment.

The application server 125 is a computer or network of computers. Although a simplified example is illustrated in FIG. 1B, typically the application server will be a server class system that uses powerful processors, large memory, and faster network components compared to a typical computing system used, for example, as a client device 110. The server typically has large secondary storage, for example, using a RAID (redundant array of independent disks) array and/or by establishing a relationship with an independent content delivery network (CDN) contracted to store, exchange and transmit data such as the asthma notifications contemplated above. Additionally, the computing system includes an operating system, for example, a UNIX operating system, LINUX operating system, or a WINDOWS operating system. The operating system manages the hardware and software resources of the application server 125 and also provides various services, for example, process management, input/output of data, management of peripheral devices, and so on. The operating system provides various functions for managing files stored on a device, for example, creating a new file, moving or copying files, transferring files to a remote system, and so on.

The application server 125 includes a software architecture for supporting access and use analytics system 100 by many different client devices 110 through network 135, and thus at a high level can be generally characterized as a cloud-based system. The application server 125 generally provides a platform for patients 111 and healthcare providers 112 to report data recorded by the sensors associated with their heart monitoring device 130.

Generally, the application server 125 is designed to handle a wide variety of data. The application server 125 includes logical routines that perform a variety of functions including checking the validity of the incoming data, parsing and formatting the data if necessary, passing the processed data to a database server 120 for storage, and confirming that the database server 120 has been updated.

The application server 125 stores and manages data at least in part on a patient by patient basis. Towards this end, the application server 125 creates a patient profile for each subject. The patient profile is a set of data that characterizes a patient 111 of the system 100. The patient profile may include identify information about the patient such as age, gender, current medications, notification preferences, and a list of non-patient subjects authorized to access to the patient profile. The profile may further specify a device identifier, such as a unique media access control (MAC) address identifying the one or more client devices 110 or heart monitoring devices 130 authorized to submit data for the patient.

The database server 120 stores data according to defined database schemas. Typically, data storage schemas across different data sources vary significantly even when storing the same type of data including cloud application event logs and log metrics, due to implementation differences in the underlying database structure. The database server 120 may also store different types of data such as structured data, unstructured data, or semi-structured data. Data in the database server 120 may be associated with subjects, groups of subjects, and/or entities. The database server 120 provides support for database queries in a query language (e.g., SQL for relational databases, JSON NoSQL databases, etc.) for specifying instructions to manage database objects represented by the database server 120, read information from the database server 120, or write to the database server 120.

The network 135 represents the various wired and wireless communication pathways between the client 110 devices, the heart monitoring device 130, the application server 125, and the database server 120. Network 135 uses standard Internet communications technologies and/or protocols. Thus, the network 135 can include links using technologies such as Ethernet, IEEE 102.11, integrated services digital network (ISDN), asynchronous transfer mode (ATM), etc. Similarly, the networking protocols used on the network 135 can include the transmission control protocol/Internet protocol (TCP/IP), the hypertext transport protocol (HTTP), the simple mail transfer protocol (SMTP), the file transfer protocol (FTP), etc. The data exchanged over the network 135 can be represented using technologies and/or formats including the hypertext markup language (HTML), the extensible markup language (XML), etc. In addition, all or some links can be encrypted using conventional encryption technologies such as the secure sockets layer (SSL), Secure HTTP (HTTPS) and/or virtual private networks (VPNs). In another embodiment, the entities can use custom and/or dedicated data communications technologies instead of, or in addition to, the ones described above.

Generally, the exact physical components used in a client device 110 will vary in size, power requirements, and performance from those used in the application server 125 and the database server 120. For example, client devices 110, which will often be home computers, tablet computers, laptop computers, or smart phones, will include relatively small storage capacities and processing power, but will include input devices and displays. These components are suitable for subject input of data and receipt, display, and interaction with notifications provided by the application server 125. In contrast, the application server 125 may include many physically separate, locally networked computers each having a significant amount of processing power for carrying out the COPD risk analyses introduced above. In one embodiment, the processing power of the application server 125 provided by a service such as Amazon Web Services™. Also in contrast, the database server 120 may include many, physically separate computers each having a significant amount of persistent storage capacity for storing the data associated with the application server.

FIG. 1B is a high-level block diagram illustrating physical components of an example computer 140 that may be used as part of a client device 110, application server 125, and/or database server 120 from FIG. 1A, according to one embodiment. Illustrated is a chipset 150 coupled to at least one processor 145. Coupled to the chipset 150 is volatile memory 155, a network adapter 160, an input/output (I/O) device(s) 165, a storage device 170 representing a non-volatile memory, and a display 175. In one embodiment, the functionality of the chipset 150 is provided by a memory controller 151 and an I/O controller 152. In another embodiment, the memory 155 is coupled directly to the processor 145 instead of the chipset 150. In some embodiments, memory 155 includes high-speed random access memory (RAM), such as DRAM, SRAM, DDR RAM or other random access solid state memory devices.

The storage device 170 is any non-transitory computer-readable storage medium, such as a hard drive, compact disk read-only memory (CD-ROM), DVD, or a solid-state memory device. The memory 155 holds instructions and data used by the processor 145. The I/O device 165 may be a touch input surface (capacitive or otherwise), a mouse, track ball, or other type of pointing device, a keyboard, or another form of input device. The display 175 displays images and other information from for the computer 140. The network adapter 160 couples the computer 140 to the network 135.

As is known in the art, a computer 140 can have different and/or other components than those shown in FIG. 1B. In addition, the computer 140 can lack certain illustrated components. In one embodiment, a computer 140 acting as server 120 may lack a dedicated I/O device 165. Moreover, the storage device 170 can be local and/or remote from the computer 140 (such as embodied within a storage area network (SAN)), and, in one embodiment, the storage device 170 is not a CD-ROM device or a DVD device.

As is known in the art, the computer 140 is adapted to execute computer program modules for providing functionality described herein. A module can be implemented in hardware, firmware, and/or software. In one embodiment, program modules are stored on the storage device 170, loaded into the memory 155, and executed by the processor 145.

III. Heart Monitoring Device
III.A. Overview

FIGS. 2A-G illustrate the heart monitoring device 130, according to some embodiments. A heart monitoring device 130 to measure heart activity of a subject includes an enclosure 205, audio microphones 210, electrodes 220, and pulse oximeters 230. The heart monitoring device 130 may additionally include any combination of other sensors, e.g., a Doppler sensor 270, a force sensor 275, a reed switch, and a plurality of movement sensors. Additionally, the heart monitoring device 130 includes components used for aiding operation of the various sensors, these components including a battery 260 and a controller (e.g., a computer 140) comprising a circuit board 280 and electronic leads 285. The enclosure 205 contains the various sensors including the audio microphones 210, the electrodes 220 and the pulse oximeters 230 on exterior surfaces of the enclosure 205 with the battery 260 and the controller residing inside the enclosure 205. The audio microphones 210 measure acoustic intensity. The electrodes 220 measure a subject's heart electrical activity. The pulse oximeters 230 measure a subject's blood oxygen level which can be used to calculate a pulse wave velocity and a blood pressure. The battery 260 provides power to the any of the sensors including the audio microphones 210, the electrodes 220, the pulse oximeters 230, the Doppler sensor 270, the force sensor 275, the plurality of movement sensors, and the controller. The controller stores and transmits data from the various sensors. In other embodiments, the heart monitoring device 130 contains any combination of the above listed components and a combination of additional sensors (e.g., a barometer, a thermometer, etc.).

III.B. Structural Design

The enclosure 205 is circular and sized to fit an average human hand with a first groove 240 located on the outer exterior surface of the enclosure 205. The enclosure 205 has a top surface and a bottom surface; where the top surface is coupled to fit a human hand, and the bottom surface is substantially flat. The first groove 240 along the top surface of the enclosure 205 is shaped and oriented so as to fit a right finger of a subject's right hand when the subject is holding the heart monitoring device 130 in their right hand, and subject's right arm is bent in front of and towards the subject's left chest to hold the heart monitoring device 130 over their heart. The first groove 240 determines an orientation of the device when held by the subject's right hand against the subject's left chest. For example in FIG. 2H, if a subject were to hold the heart monitoring device 130 with the subject's right hand 290 such that the subject's right index finger 292 keys into the first groove 240, the orientation of the heart monitoring device 130 against the subject's chest is restricted to a desired range of orientations.

The enclosure 205 may include additional grooves, one example of which is second groove 250. The second groove 250 adds precision in determination of an orientation of the heart monitoring device 130 when held by the subject's right hand. The second groove 250 is coupled to the top surface of outer exterior surface of the enclosure 205, in accordance with an embodiment. The second groove 250, similar to the first groove 240, is shaped and oriented so as to fit another right finger of the subject's right hand when the subject is holding the heart monitoring device 130 in their right hand, and the subject's right arm is bent in front of and towards the subject's left chest to hold the heart monitoring device 130 over their heart. In one embodiment, the second groove 250 is keyed to fit a subject's right thumb, such that when the right thumb keys into the second groove 250 in tandem with a right index finger keying into the first groove 240, the positioning of the heart monitoring device against the subject's chest is restricted. In some embodiments, utilizing the first groove 240 and the second groove 250 in tandem provides an increase in restriction of the positioning of the heart monitoring device 130. In an additional embodiment, the enclosure 205 includes an additional groove keyed to fit a subject's right hand palm on a top surface of the enclosure 205.

The three electrodes 220 of the heart monitoring device 130 for capturing EKG data are positioned so as to capture two different electric potential vectors of heart activity. Two of the electrodes 220 are placed on the bottom surface of the enclosure 205 along a diameter 175 of the enclosure 205 shown in FIG. 2C. A third electrode of the electrodes 220 is placed on a side of the enclosure 205. In some embodiments, the third electrode is placed in a groove, e.g., the second groove 250 configured to fit a subject's right thumb. The placement of the electrodes 220 provides for a two-dimensional reading of the heart's electrical activity, and the desired orientation is a range of angles whereby both of those vectors are distinct from each other to at least some degree. Further description of the electrodes 220 will be further described in Section III.D. EKG Monitoring.

The placement of the pulse oximeters 230 in the groove 240 of the heart monitoring device 130 insures a proper orientation of the heart monitoring device 130 prior to monitoring heart activity. The pulse oximeters 230 can detect if a subject's finger is in contact with the pulse oximeters 230. If so, the subject's right index finger is resting in the groove 240. When the subject also holds the heart monitoring device 130 against the subject's chest with the subject's right hand, the heart monitoring device 130 is now restricted to the limited rotation of the subject's arm. Thus, the groove 240 that holds the pulse oximeters 230 performs multiple functions in a constrained, ergonomic physical package. The pulse oximeters' 230 function will be described further in Section III.E. Pulse Oximeter.

The audio microphones 210 detect ambient sounds and pulses of the subject's heart. A first audio microphone 210 is placed on the top surface of the enclosure 205 and is not in contact with the subject's skin, as shown in FIG. 2A. The first audio microphone 210 records an acoustic intensity of ambient sound. A second audio microphone 210 is placed on the bottom surface of the enclosure 205 and is in contact with the subject's chest when the heart monitoring device 130 is held against the subject's chest. The second audio microphone 210 records an acoustic intensity corresponding to pulses of the subject's heart.

The Doppler sensor 270 measures a Doppler shift of blood flow. Referring to FIG. 2E, the Doppler sensor 270 is placed on the bottom surface of the enclosure so as to couple to the subject's chest when the heart monitoring device 130 is held by the subject against the subject's chest. The Doppler sensor 270 includes two transducers placed a distance apart from one another configured to transmit and receive acoustic signals. The operation of the Doppler sensor 270 will be further described in Section III.F. Doppler Sensor.

In some embodiments, the heart monitoring device 130 includes other sensors. In one embodiment, a force sensor 275 is coupled within the enclosure 205 to one of the electrodes 220, as shown in FIGS. 2E & 2F. The force sensor 275 is used to measure a force applied onto the electrode to which the force sensor 275 is coupled. The force sensor 275 will be described further in Section III.G.i. Force Sensor. In another embodiment, a reed switch is coupled to an interior portion of the enclosure 205. The reed switch may be used to detect a presence of a magnetic field which may be used to signify proximity to an external object. The reed switch will be described further in Section III.G.ii. Reed Switch. In yet another embodiment, one or more inertial measurement units (IMUs) may be used to record movement of the heart monitoring device 130. The IMUs will be described further in Section III.G.iii. Inertial Measurement Units.

III.C. Proper Orientation

In FIG. 2H, the first groove 240 and the second groove 250 both help restrict the positioning of the heart monitoring device 130. In this illustration, the subject has two phalanges keyed into the two grooves—the subject's right index finger 292 keys into the first groove 240 and the subject's right thumb 294 keys into the second groove 250.

More specifically, the desired range of orientations of the heart monitoring device 130, for appropriate capture of data by the electrodes 220, is approximately where the subject's right hand would be oriented without straining or unnatural rotation of the wrist when one finger of the right hand is inserted in one or more of the grooves (e.g., 240 and 250). Due to differences in body shape, particularly arm length, among the human population, and further due to the fact that invariably some subjects will hold the heart monitoring device 130 with some amount of wrist angle away from neutral, the exact desired angle for positioning of the heart monitoring device 130 and holding of the right arm/right hand over the chest will have an acceptable range of variation. This is anticipated in the heart monitoring device 130 design, particularly in the arrangement of electrodes 220 of the heart monitoring device 130. The range of desired orientations as dictated by the one or more finger grooves 240 & 250 relative to the positions of the electrodes 220 is chosen so that the heart monitoring device 130 is able to capture both of these vectors of data regardless of the shape/size of the subject, and thus the heart monitoring device 130 is able to operate appropriately for the entirety of the human population.

III.D. EKG Monitoring

The electrodes 220 measure voltage differences across an electrical circuit which includes a subject's heart. When the enclosure 205 is in the proper orientation, the three electrodes 220 are configured such that a right thumb electrode 132 is coupled to the subject's right thumb and two chest electrodes 136 & 138 are coupled to subject's chest shown in FIGS. 3A & 3B. An upper chest electrode 136 is closer towards the subject's head; whereas, a lower chest electrode 138 is closer towards the subject's waist. The three electrodes 220 measure voltage differences across two electrical circuits inclusive of the subject's heart: one electrical circuit is completed with the upper chest electrode 136 and the right thumb electrode 132; a second electrical circuit is completed with the lower chest electrode 138 and the right thumb electrode 132.

Figure 3A:
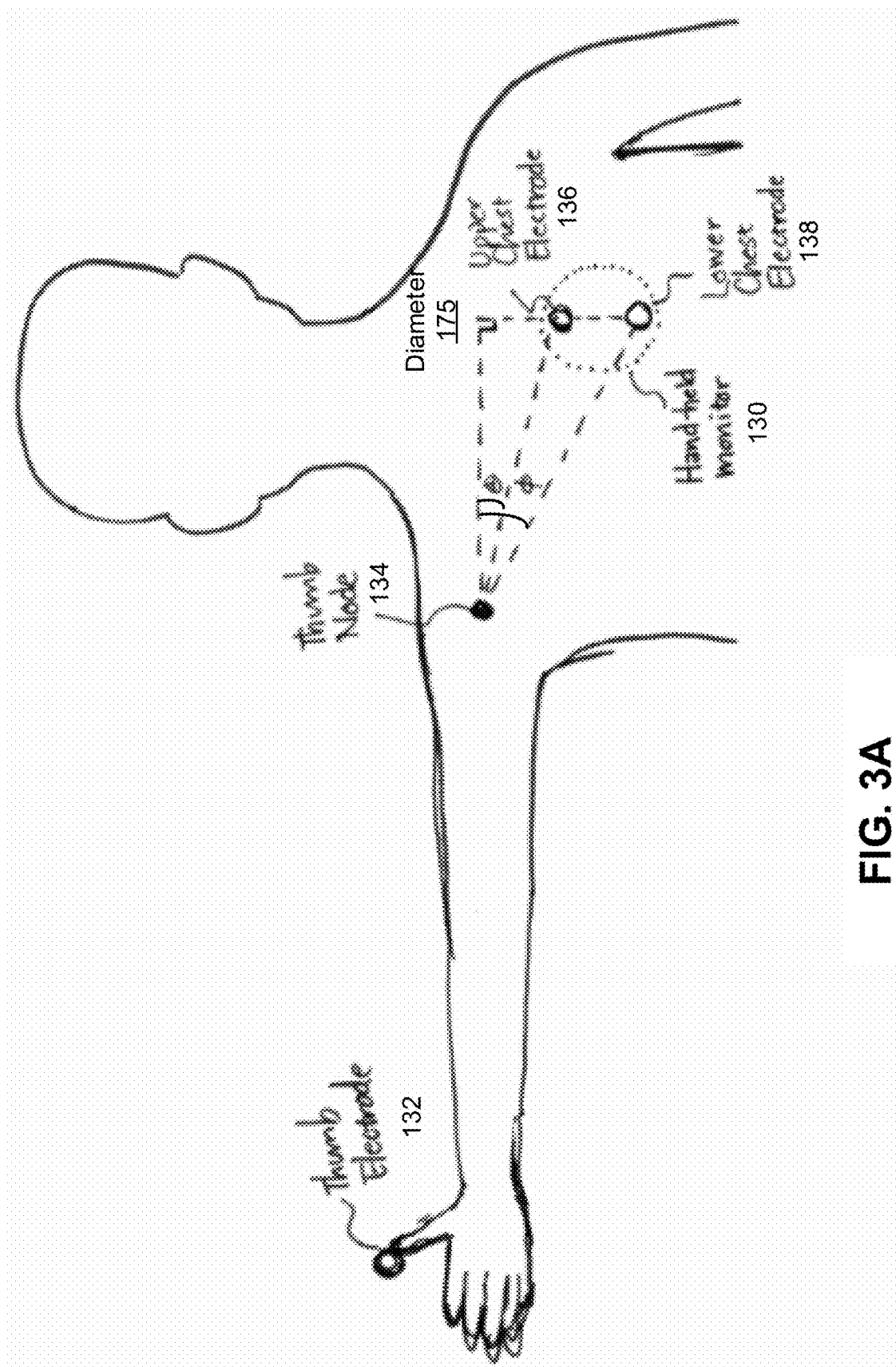
FIG. 3A illustrates a lead configuration of the heart monitoring device, according to an embodiment.

Two of the three electrodes 220 are configured to the bottom surface of the enclosure 205 along a diameter 175 of the enclosure 205 positioned relative to a subject as shown in FIG. 3A. Wherein the diameter 175 is approximately parallel to the subject's spine when the enclosure 205 is within the desired range of orientations. A right thumb electrode 132 of the electrodes 220 is configured where the subject's right thumb lies in the orientation of the enclosure 205, which may be located in second groove 250. With the diameter 175 and the perpendicular from the right shoulder node 134, two angles θ and φ can be defined as angles of depression from the perpendicular in defining the two vectors, one to the upper chest electrode 136 and one to the lower chest electrode 138. The acceptable range of orientation of the device may, for example, be described as an angular range of plus or minus some number of degrees of rotation away from a "center" angle, defined with respect to the angles θ and φ, and/or with respect an angle measured from the center of the device (not shown).

Figure 3B:
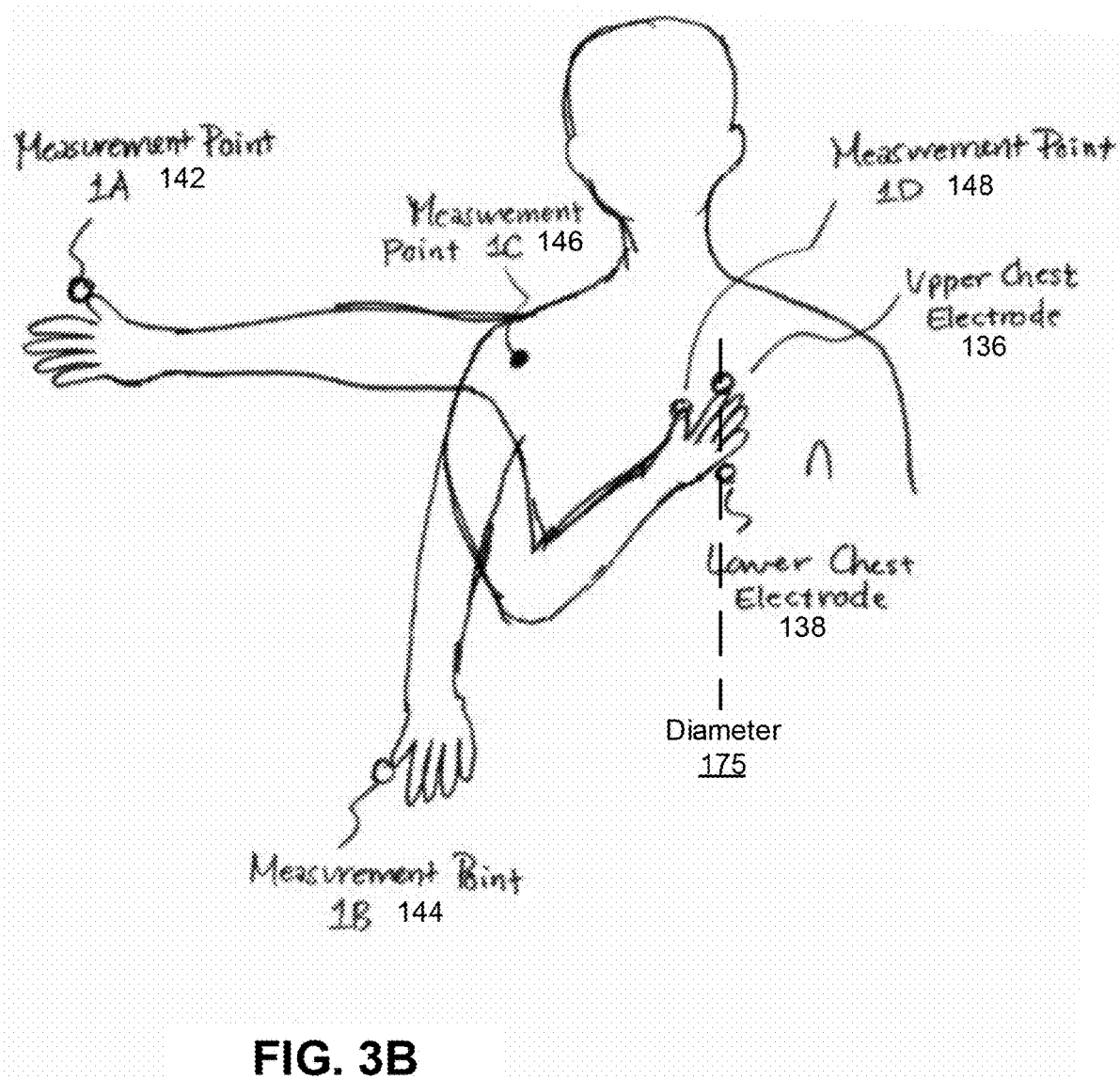
FIG. 3B illustrates a proper orientation of the heart monitoring device in relation to a subject's chest, according to an embodiment.

In FIG. 3B, the two completed circuits create two vectors which both span from the shoulder measurement point 1C 146 to each corresponding chest electrode 136 & 138. FIG. 3B shows how the right thumb electrode 132 when the heart monitoring device is in proper orientation at measurement point 1D 148 is synonymous with the subject outstretching his/her arm. Both circuits run along the subject's arm, but from the shoulder measurement point 1C 146 do the two electrical circuits become distinct vectors. The voltage difference measurements over time across both electrical circuits correspond to these two distinct vectors across the subject's heart. The two vectors provide a basis for a 2D mapping through linear combination 300 of the two vectors described further in FIG. 3F. From the 2D mapping, the heart monitoring device 130 can transform the 2D mapping 300 into a 12 lead electrocardiogram.

Figure 3C:
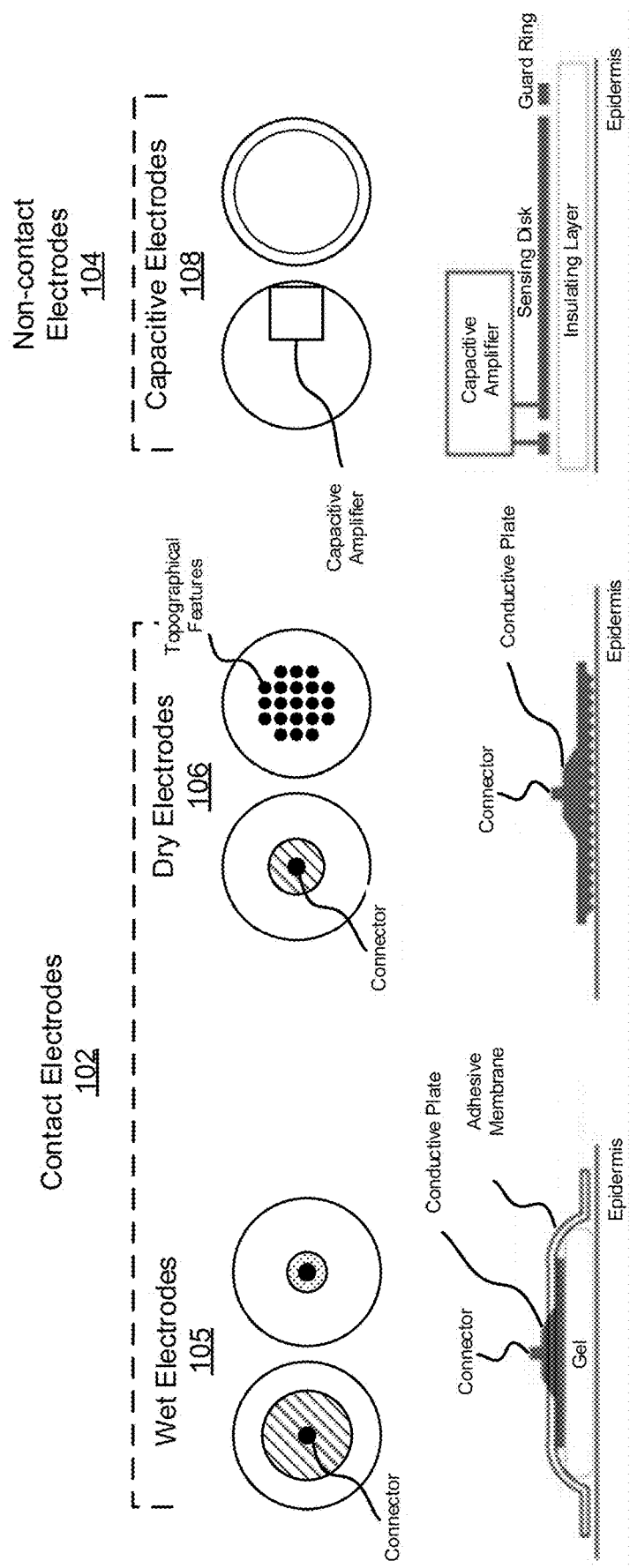
FIG. 3C illustrates construction of different types of electrodes, according to an embodiment.
Figure 3D:
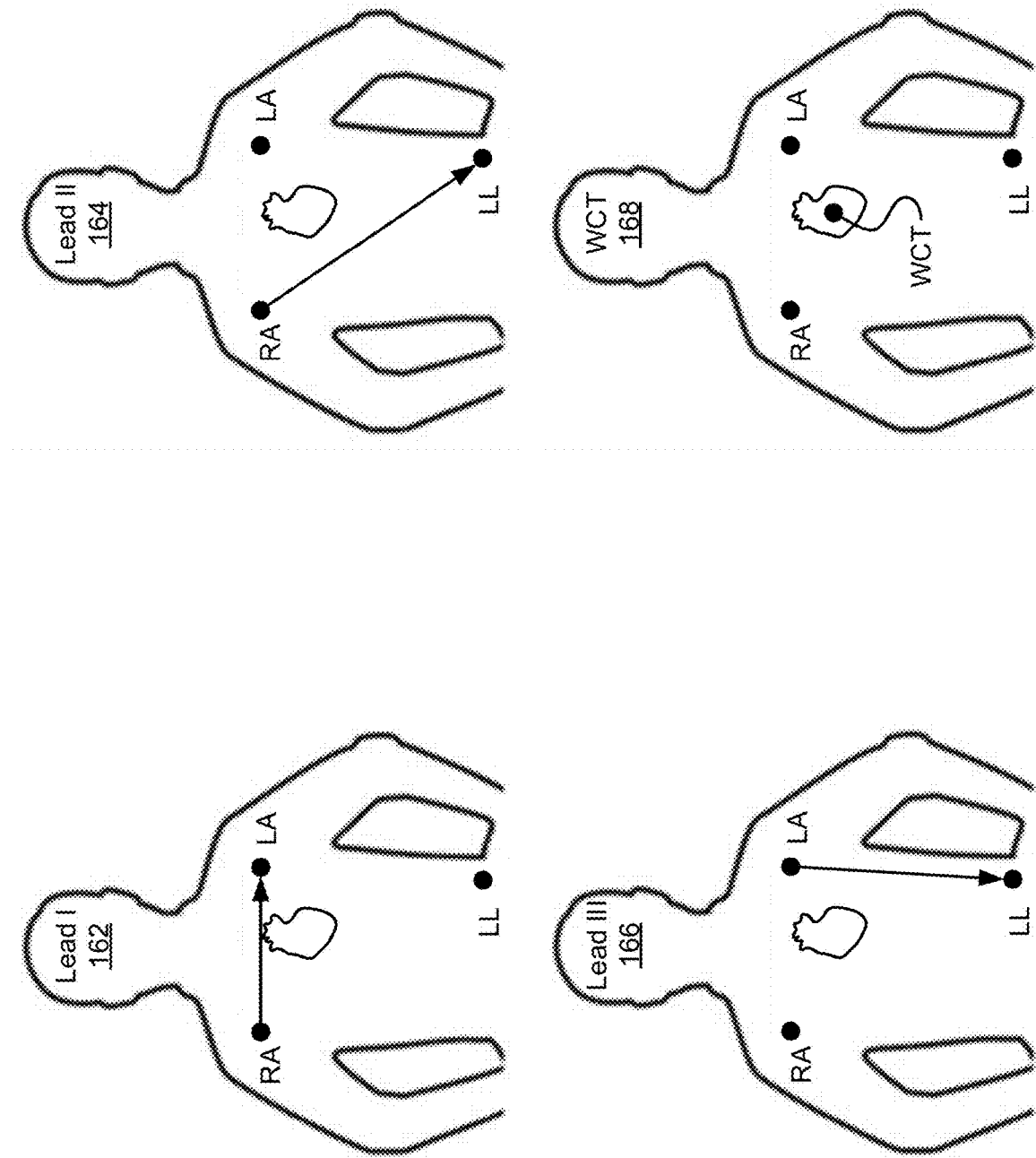
FIG. 3D illustrates leads used in measuring heart electrical activity, according to an embodiment.
Figure 3E:
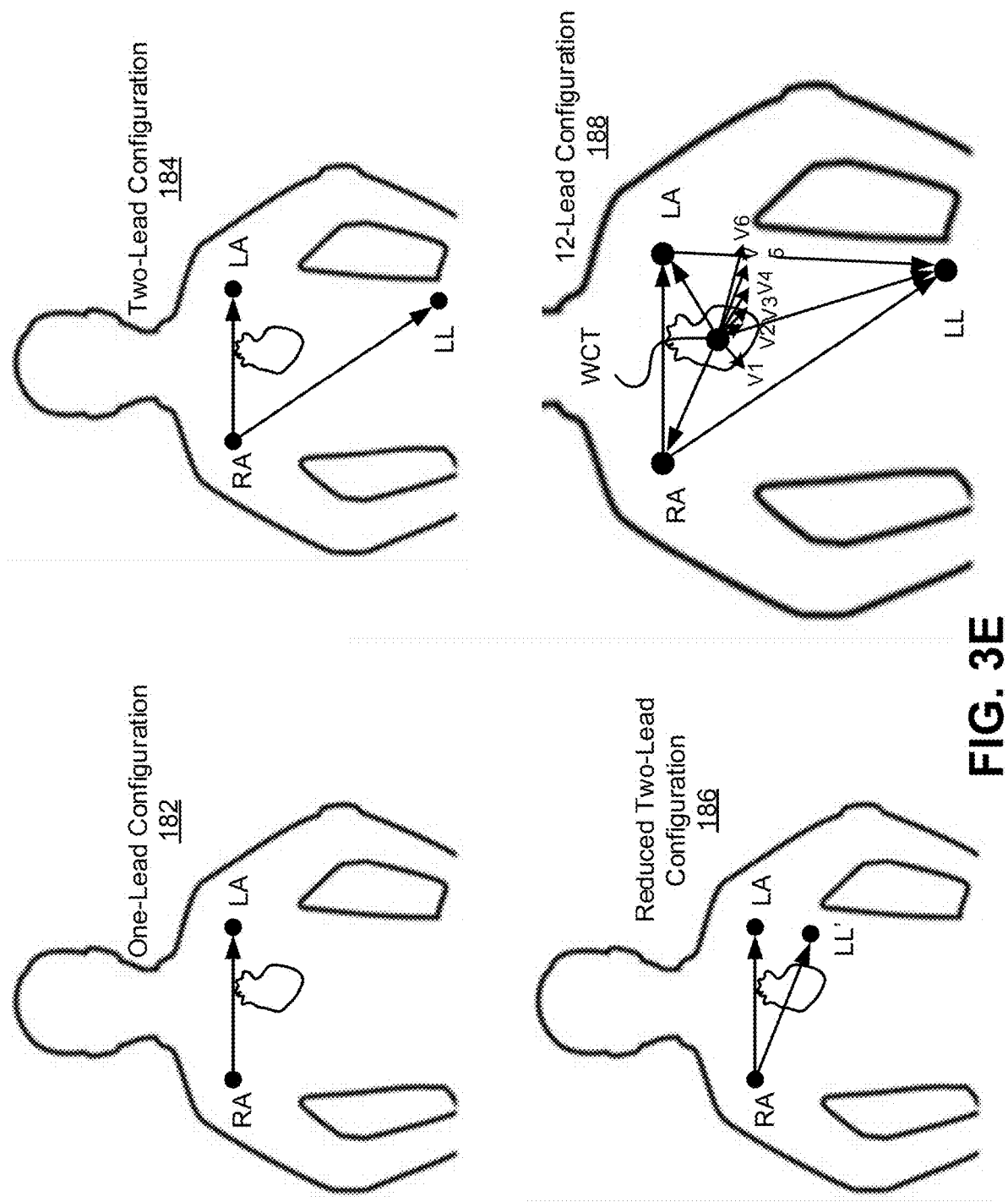
FIG. 3E illustrates lead configurations for measuring heart electrical activity, according to an embodiment.
Figure 3F:
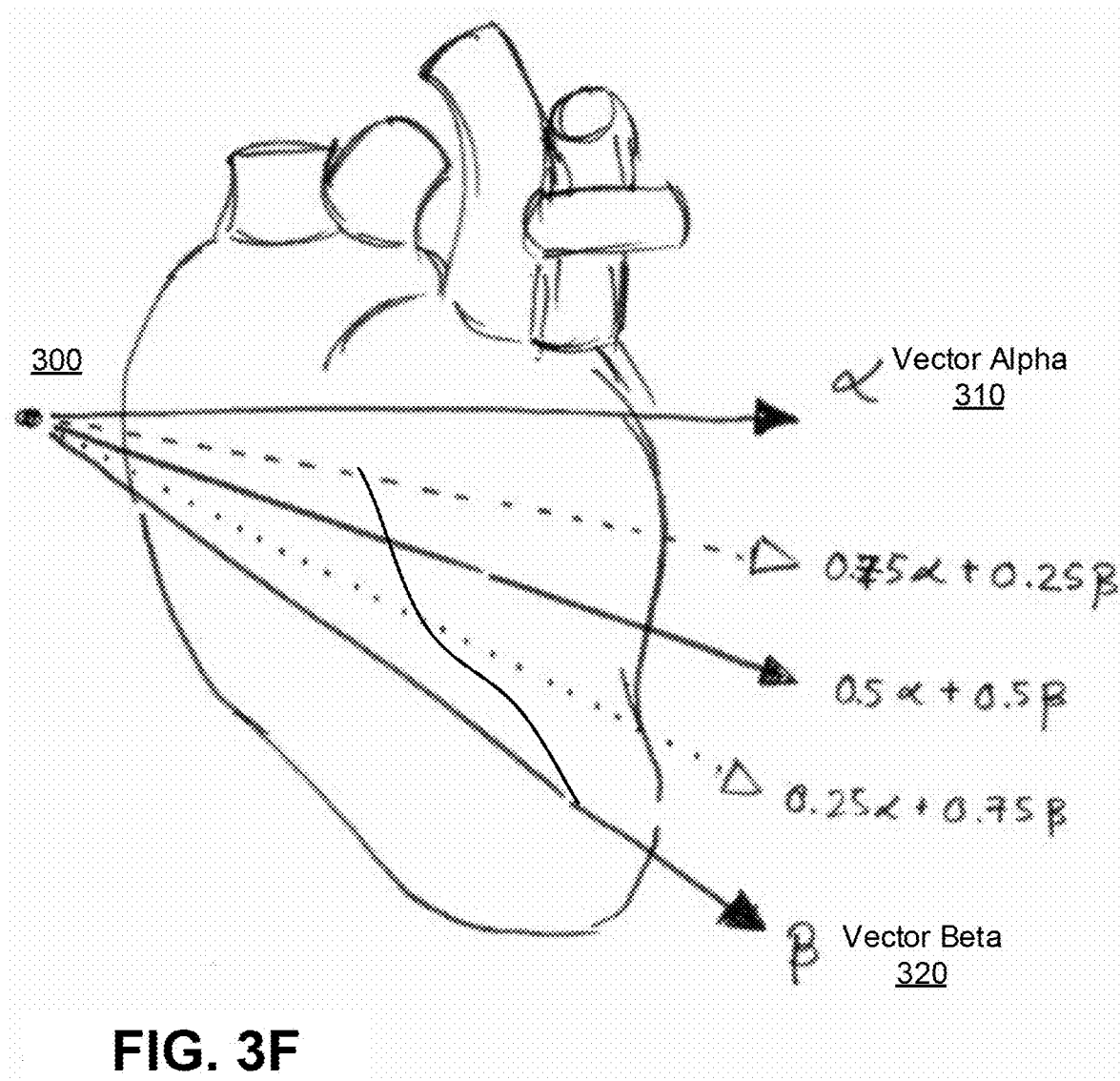
FIG. 3F illustrates a calculation of a scalar gradient field based on measurements by the heart monitoring device, according to an embodiment.

The electrodes 220 may be constructed in different ways. Referring now to FIG. 3C, FIG. 3C shows various types of electrodes that may be used in the heart monitoring device 130 including contact electrodes 102 and non-contact electrodes 104. Within contact electrodes 102, there are wet electrodes 105 and dry electrodes 106. Non-contact electrodes 104 are typically capacitive electrodes 108. Wet contact electrodes 105 have a connector which provides electrical power and a conductive plate. Application of each wet electrode 105 comprises 1) shaving clean a portion of a subject's skin so as to remove hair and dead skin which can act as insulators defined as artifacts; 2) applying a sticky, wet ionic gel for increasing contact area between the conductive plate and the skin; 3) applying the wet contact electrode 105 with the conductive plate on top of the gel; and 4) applying an adhesive sticker or other form of adhesion to the wet contact electrode 105. Dry contact electrodes 106 have a connector which provides electrical power and a conductive plate. Dry contact electrodes 106 couple to a subject's skin with an optional step of applying forms of adhesion. As dry contact electrodes 106 comprise rigid conductive plates, without aid of a gel the conductive plates may lose contact when the subject moves around which are defined as movement artifacts. To maximize contact area, some dry contact electrodes 106 utilize topographic features to improve contact area between the conductive plate and the subject's epidermis. Non-contact electrodes 106 such as capacitive electrode 108 typically have a capacitive amplifier, a sensing disk, and a guard ring. Without placing the sensing disk in contact with the epidermis, the sensing disk and the subject's epidermis are separated by an insulating layer configured as a dielectric thus providing capacitance to the capacitive electrode 108, wherein variations in capacitance provide capabilities of measuring heart electrical activity.

In one embodiment, the electrodes 220 are dry electrodes 106. According to this embodiment, the electrodes 220 are dry conductive surfaces. The electrodes 220 are circular on the order of 1 cm in diameter. The electrode 220 is generally flat with the topographical features constructed as an array of bumps on the order of 2 mm in height. The electrode 220 is constructed with silver or silver chloride so as to provide minimal resistance at the interface between a subject's skin and the electrode 220. The application of the electrodes 220 utilizes direct contact with a subject's skin surface. The powder-coated electrodes 220 improve contact with the skin by allowing the skin to mold around the plastic bumps. The electrodes 220 conduct electrical current to measure voltage differences between two nodes of an electrical circuit. In this embodiment, the electrodes 220 remove the possible discomfort of the sticky, wet gels applied with wet electrodes 105.

The heart monitoring device 130 establishes a multidimensional reading of the heart's electrical activity. Referring now to FIGS. 3D & 3E, these figures illustrate various leads and lead configuration used in measuring heart electrical activity. To establish a multidimensional reading, ideally, three or more electrodes complete two or more electrical circuits across the heart so as to provide a plurality of electric potential vectors across the heart. The two or more electrical circuits are non-coincidental such that they provide non-collinear electric potential vectors. With three contact points completing two non-coincidental circuits, there is a triangle of three electric potential vectors, at least two of which are measured by the EKG monitor with an option to calculate a third with Kirchhoff's Law. In FIG. 3D, there is a first electric potential vector defined as Lead I 162 measured from a circuit completed across a subject's right arm (RA) to the subject's left arm (LA). There is a second electric potential vector defined as Lead II 164 measured from a circuit completed across the subject's right arm (RA) to the subject's left leg (LL). There is a third electric potential vector defined as Lead III 166 measured from a circuit completed across the subject's left arm (LA) to the subject's left leg (LL). Additionally, there may be a derived electrode, namely a Wilson Central Terminal (WCT) as shown in FIG. 3D. The WCT is calculated as a position vector defined as a third of a vector summation of the three electric potential vectors.

Various lead configurations may be used determining combinations of the leads described above. With only two electrodes completing a circuit across the subject's right arm (RA) to the subject's left arm (LA) defines a one-lead configuration 182, as shown in FIG. 3E. With three electrodes coupled to the subject's right arm (RA), the subject's left arm (LA), and the subject's left leg (LL) defines a two-lead configuration 184, as shown in FIG. 3E. A reduced two-lead configuration 186 takes the two-lead configuration 184 and moves the electrode coupled to the left leg (LL) to be on the subject's torso such as LL' in FIG. 3E, below the electrode coupled to the left arm (LA). In one embodiment, the heart monitoring device 130 is configured as a reduced two-lead configuration 186 measuring Lead I from the right thumb electrode 132 to the upper chest electrode 136 (as shown in FIG. 3A) and Lead II from the right thumb electrode 132 to the lower chest electrode 138. Additionally for a 12-lead configuration 188, utilizes a derived electrode, namely a Wilson Central Terminal (WCT) as shown in FIG. 1G. The WCT establishes a central node with which to calculate additional electric potential vectors providing even greater insight into the subject's heart. From the WCT, there may be additional electric potential vectors which can be calculated with one or more electrodes coupled to the subject's mid-torso. For the 12-lead configuration 188, there are six additional electrodes coupled to the chest labeled V1, V2, V3, V4, V5, and V6. This allows for a total of twelve electric potential vectors to be measured or calculated.

FIG. 3 illustrates the calculation of a scalar gradient field based on measurements of the heart monitoring device 130, according to an embodiment. The heart activity is a scalar gradient field. As measured by the heart monitoring device 130, two closed electrical circuits provide two non-collinear vectors $\alpha$ and $\beta$. The two vectors labeled $\alpha$ and $\beta$ correspond to the first circuit, completed by the thumb electrode 132 and the upper chest electrode 136, and the second circuit, completed by the thumb electrode 132 and lower chest electrode 138, in accordance with an embodiment. The two vectors $\alpha$ and $\beta$ form a basis for the scalar gradient field such that from two vectors, the entire scalar gradient field can be generated. The two vectors $\alpha$ and $\beta$ can also be normalized such that the basis is normal. In the illustration, positive linear combinations 300 of α and β determine 3 vectors. More generally, a number of vectors can be determined from the linear combination 300 of α and β to provide the entire scalar gradient field of the heart.

III.E. Pulse Oximeter

Figure 4A:
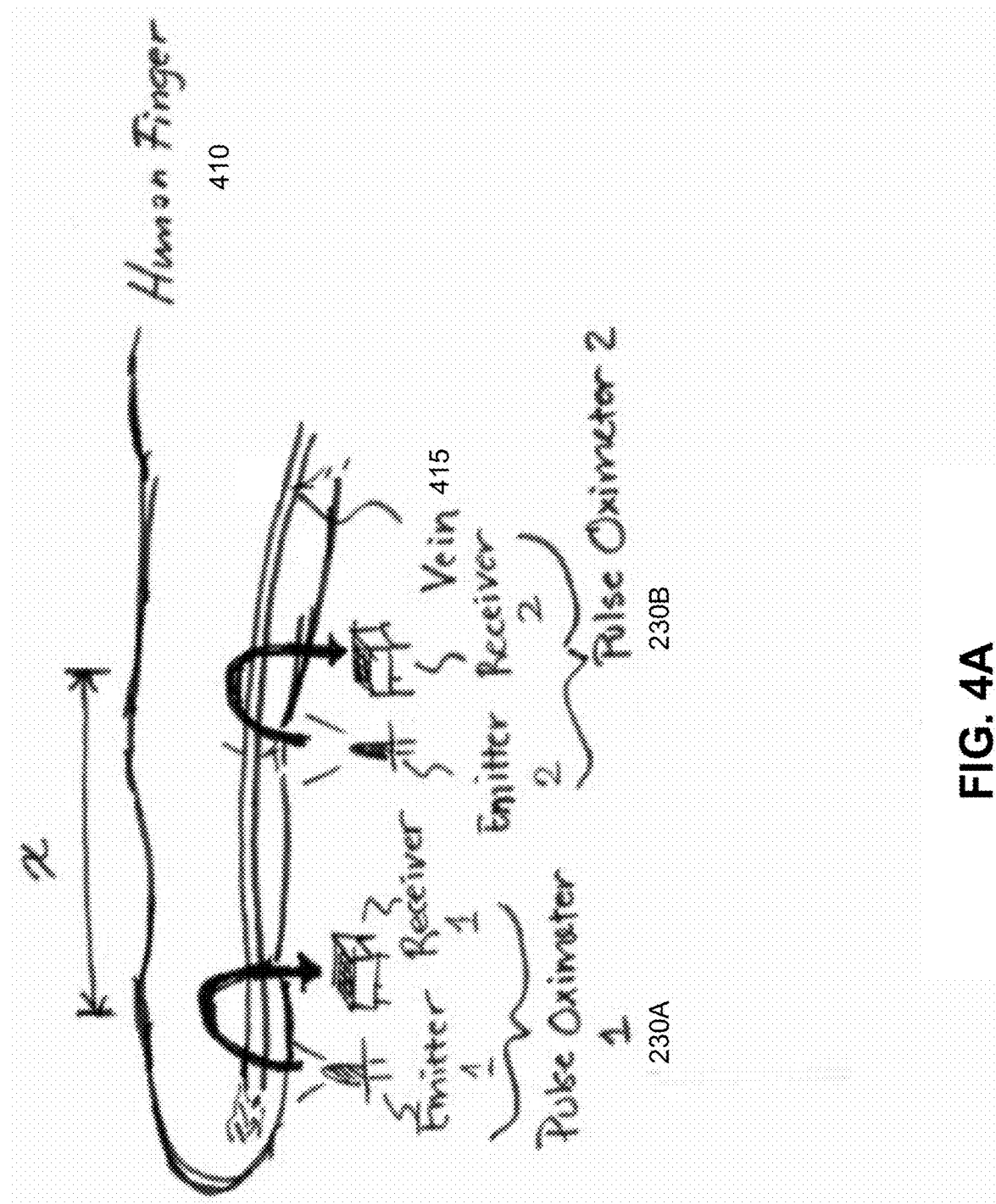
FIG. 4A illustrates a placement of the pulse oximeters of the heart monitoring device of FIG. 2A in relation to a subject's finger, according to an embodiment.
Figure 4B:
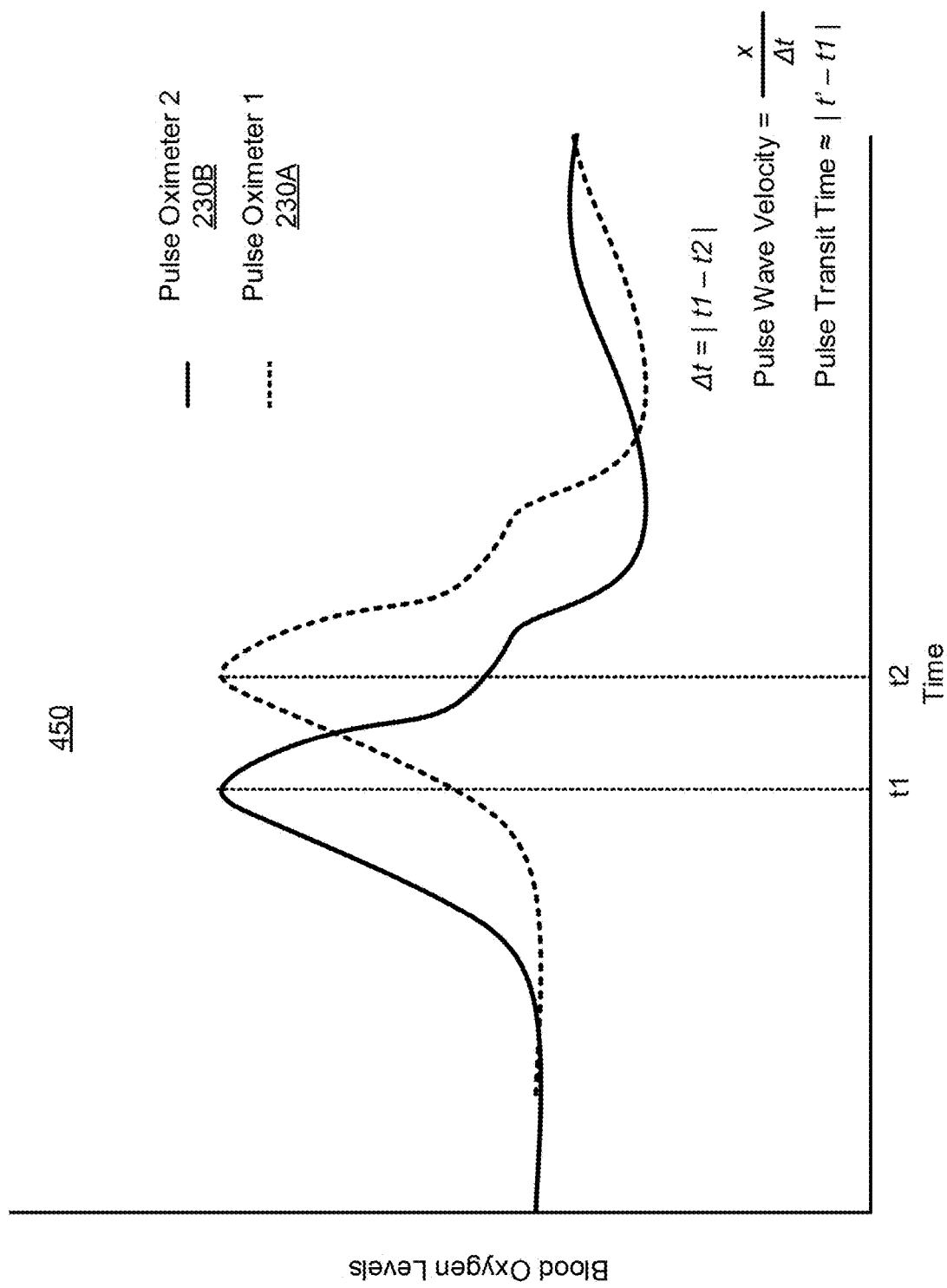
FIG. 4B illustrates a calculation of Pulse Wave Velocity (PWV) and/or Pulse Transit Time (PTT) based on measurements by the heart monitoring device, according to an embodiment.

FIGS. 4A and 4B illustrates the calculation of Pulse Wave Velocity (PWV) and Pulse Transit Time (PTT) based on measurements of the heart monitoring device 130, according to one embodiment. Two pulse oximeters 230 labeled pulse oximeter 1 230A and pulse oximeter 2 230B are coupled to measure at two different positions along a human finger 410. The pulse oximeters 230 measure blood flowing in a vein 415 of the human finger 410. Pulse oximeter 230B is located closer to the human heart than the pulse oximeter 230A. Due to the relative proximity of pulse oximeter 230B to the heart, pulse oximeter 230B is first to register a pulse wave. Sometime after, pulse oximeter 230A registers the pulse wave. This delay is shown in a chart 450 of blood oxygen levels over time measured by pulse oximeter 230A and pulse oximeter 230B in FIG. 4B.

The pulse oximeters 230 comprise a light emitter and a light receiver. When the pulse oximeter is in contact with a subject's skin, the light emitter shines light into the subject. A wavelength of light is reflected back from the subject and corresponds to an amount of oxygen present in the subject's blood. The light receiver records the wavelength of light reflected back to determine the oxygen present in the blood. The measurements over time reveal pulse waves with peaks in oxygen presence as wavefronts of the pulse waves. In FIG. 4B, the wavefront of the pulse wave measured by pulse oximeter 2 230B occurs at time t1 and the wavefront of the pulse wave measured by pulse oximeter 1 230A occurs at time t2. The difference in t2 and t1 is denoted as Δt.

The placement of the two pulse oximeters 230 at a fixed distance x in the first groove 240 of the enclosure 205 (or elsewhere on the device, in other embodiments) provides precise measurements of a pulse wave velocity of the subject. The fixed distance x between the two pulse oximeters 230 provides the pulse oximeters the ability to record a temporal difference for the pulse wave's wavefront to translate the fixed distance x. Without knowing the fixed distance x, the heart monitoring device 130 cannot compute precise measurements given an uncontrolled variance in a distance between the pulse oximeters measuring the blood flow. The fixed distance x of the two pulse oximeters 230 allows for normalization of PWV and blood pressure calculations by the heart monitoring device 130 across subjects. The PWV is calculated from the fixed distance x and time difference between wavefront measurements as Δt. The PWV is calculated as the division of the fixed distance x by the time difference Δt. The PTT describes a duration of time that occurs when a pulse is transmitted from the heart to a location of the body. The PTT may be calculated subtracting a peak time recorded in the EKG data and a peak time measured by the pulse oximeters 230. Blood pressure can be determined by a transformation of the ratio of PTT to PWV.

Figure 4C:
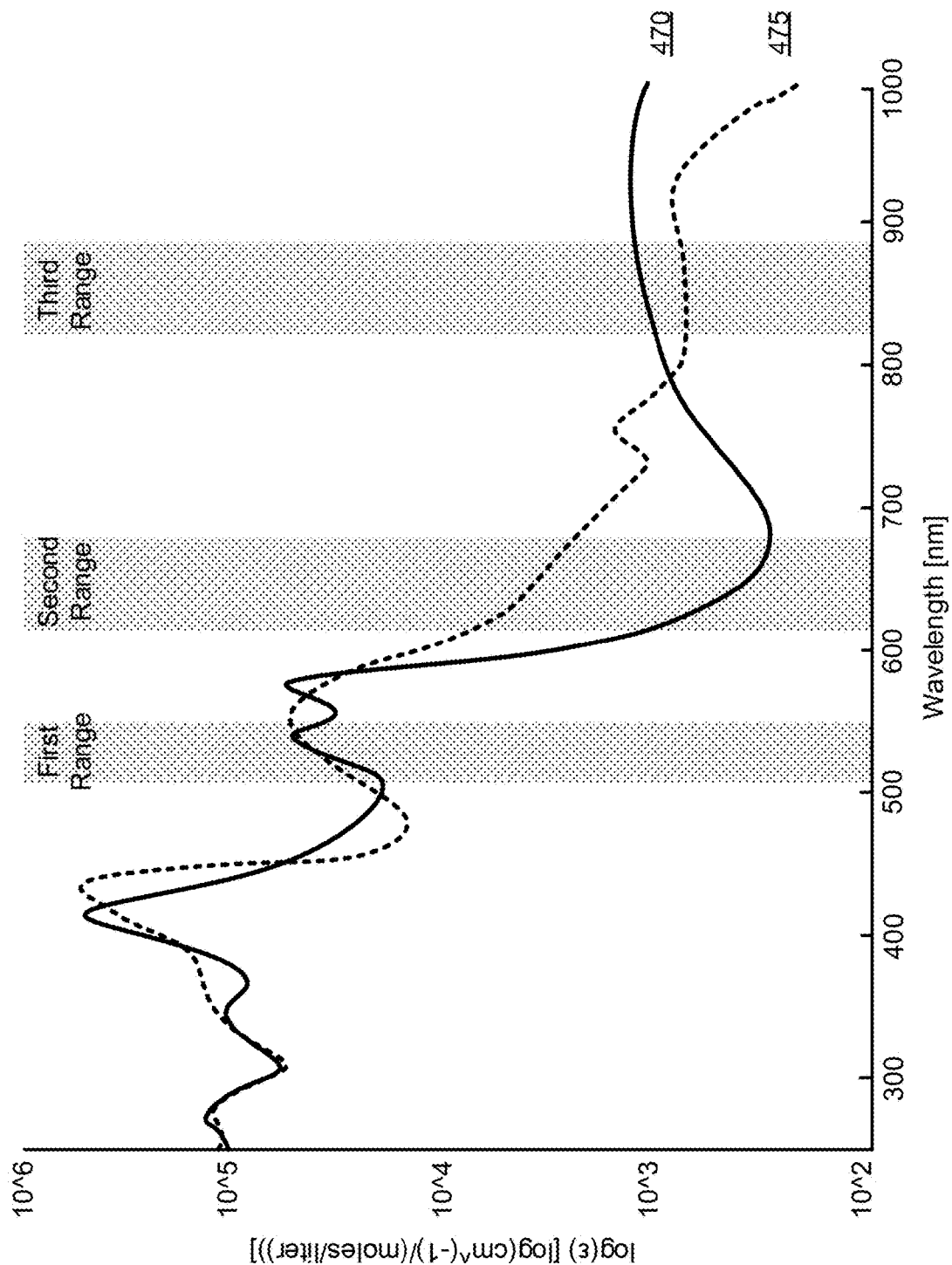
FIG. 4C illustrates a graph showing absorption of oxygenated Hemoglobin and deoxygenated Hemoglobin over a range of wavelengths of light, according to an embodiment.

FIG. 4C is a graph showing absorption of oxygenated Hemoglobin 470 and deoxygenated Hemoglobin 475 over a range of wavelengths of light. In this illustration, three ranges of light wavelengths are highlighted—a first range from 510 nm to 550 nm; a second range from 620 nm to 680 nm; and a third range from 830 nm to 990 nm. In the first range, oxygenated Hemoglobin 470 and deoxygenated Hemoglobin 475 have similar absorptions. In the second range, deoxygenated Hemoglobin 475 has overall higher absorption than oxygenated Hemoglobin 470 meaning that oxygenated Hemoglobin 470 would reflect more light in the second range than would deoxygenated Hemoglobin 475. In the third range, oxygenated Hemoglobin 470 has overall higher absorption than deoxygenated Hemoglobin 475 meaning that deoxygenated Hemoglobin 475 would reflect more light in the third range than would oxygenated Hemoglobin 470. The reflectivity of these various ranges proves useful when using pulse oximeters 230. The pulse oximeters 230 can be configured to emit and receive light over various ranges to target measuring deoxygenated blood or oxygenated blood.

III.F. Doppler Sensor

The Doppler sensor 270 measures a Doppler shift of blood flow. The Doppler sensor 270 includes two transducers placed a distance apart from one another. In one embodiment, the transducers are piezoelectric transducers that operate based on a dependence between deformation and electric potential. In other embodiments, other types of transducers are used. One transducer is configured as a transmitter which vibrates the chest wall at a transmission frequency over a time period. In implementations with piezoelectric transducers, the transmitter applies a wave function of electric potential to the piezoelectric element thereby vibrating the chest wall at the transmission frequency (e.g. ~3 MHz). The other transducer is configured as a receiver for measuring vibration of the chest wall at a receiving frequency over the time period. In implementations with piezoelectric transducers, the receiver measures an electric potential signal of the receiving frequency (e.g. ~3 MHz) over the time period based on the deformation of the piezoelectric element.

Figure 5:
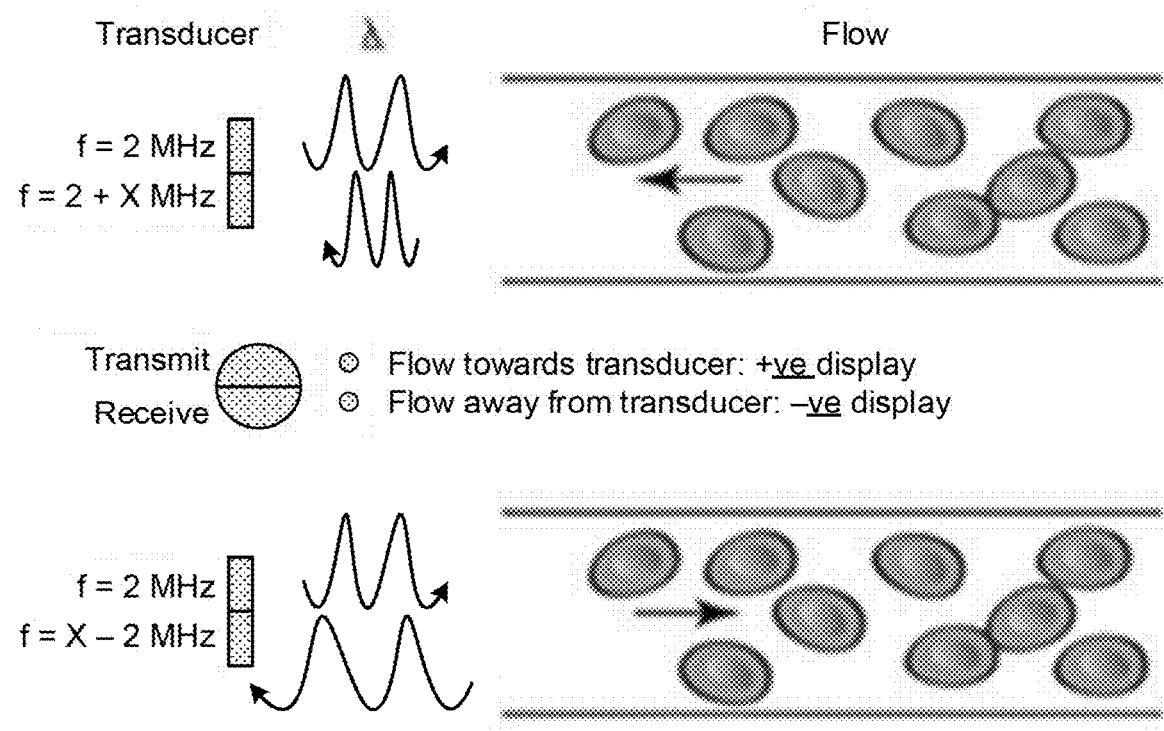
FIG. 5 illustrates a calculation of blood flow based on Doppler shift signal from a Doppler sensor, according to an embodiment.

The difference between the receiving frequency and the transmission frequency is defined effectively as a Doppler shift. The Doppler shift may be calculated with a variety of demodulation techniques including but not limited to analog demodulation with a discrete integrated component and algorithmic approaches implemented on the digital signal processing by the computer controller. The Doppler shift over the time series is influenced by movement of tissue or blood in the subject below the Doppler sensor 270. Of interest is the Doppler shift that corresponds to blood flow in the subject. Referring now to FIG. 5, the Doppler sensor 270 may determine a velocity of blood flow based on the Doppler shift signal. When taking the differential between the receiving frequency and the transmission frequency, positive differentials correspond to blood flow towards the receiver with the magnitude of the differential corresponding to speed of the blood flow. Conversely, negative differentials correspond to blood flow away from the receiver with the magnitude of the differential corresponding to speed of the blood flow.

III.G. Additional Sensors

III.G.I. Force Sensor

The force sensor 275 detects a force applied on an electrode to which the force sensor 275 is coupled. As the subject presses the heart monitoring device 130 against the subject's chest, the force used to hold the heart monitoring device 130 against the subject's chest translates to a force on the chest electrodes 136 & 138. The force sensor 275 being coupled to one of the chest electrodes 136 & 138 measures a pressure on the chest electrode to which the force sensor 275 is coupled which can be recorded as pressure data. If the force sensor 275 detects too small of a pressure on the chest electrode to which the force sensor 275 is coupled, then the force sensor 275 may report a movement artifact, under the assumption that the low pressure of attachment implies that the device is either not physically coupled to the chest, or is only loosely coupled and is possibly sliding along the chest surface.

In one implementation, the force sensor 275 operates using a force-sensitive resistor that has a dynamic resistance based on applied forces. As the force to hold the heart monitoring device 130 against the subject's chest affects the electrical voltage reading by the electrodes 220. In additional embodiments, additional force sensors 275 may be coupled to all electrodes 220 including the two chest electrodes 136 & 138 and the thumb electrode 132.

III.G.II. Reed Switch

Figure 6:
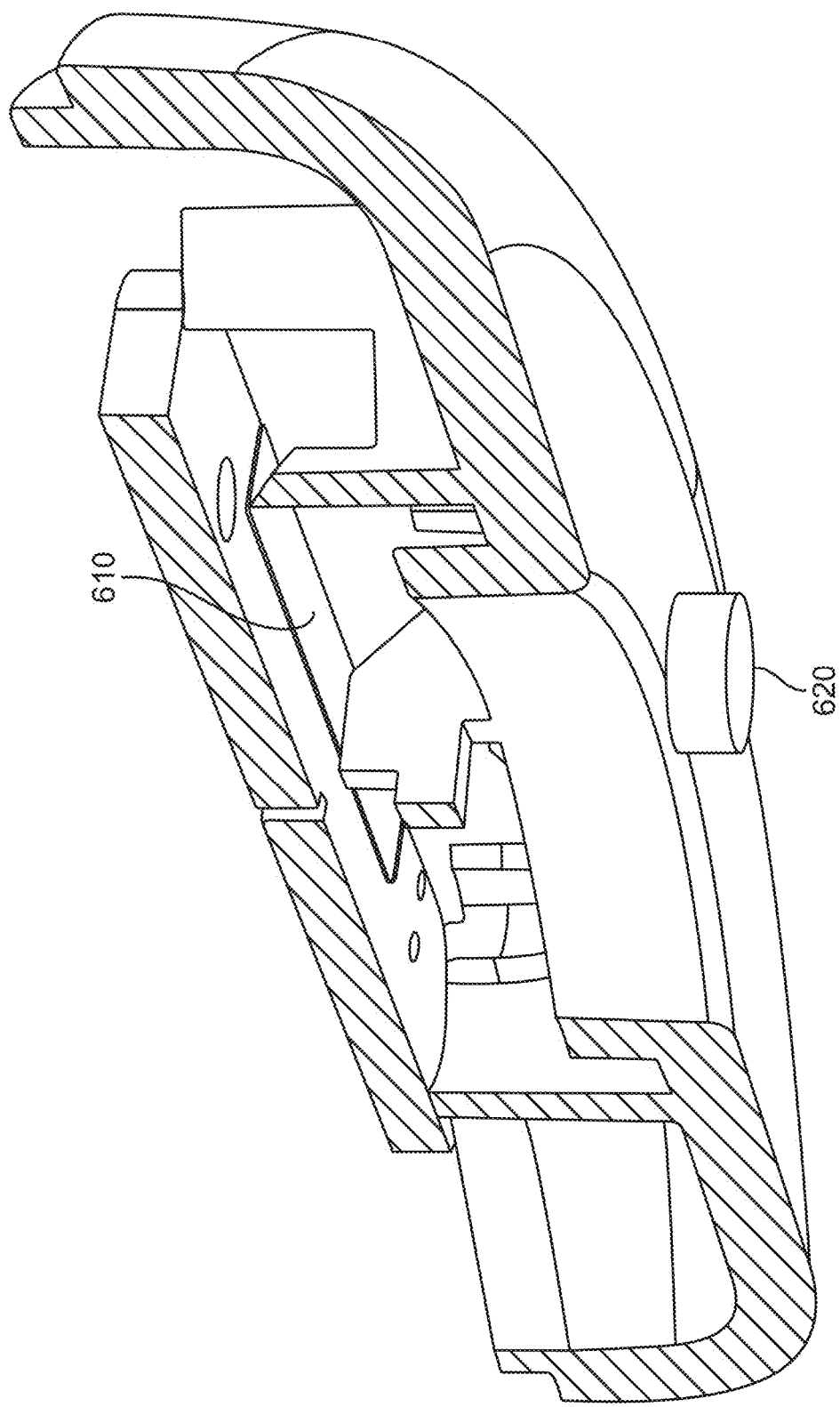
FIG. 6 illustrates a magnet and a reed switch on the heart monitoring device, according to an embodiment.

Now referring to FIG. 6, the reed switch 610 detects movement of the heart monitoring device in relation to the magnet 620. The reed switch 610 is configured to complete a circuit based on a presence of a magnetic field greater than a threshold magnetic field. The magnet 620 may be coupled to an external component. If the heart monitoring device 130 is within a proximity of the magnet 620 such that the magnetic field from the magnet 620 engages the reed switch 610 to complete the circuit, then heart monitoring device 130 detects proximity of the magnet 620. In one embodiment, the external component is a base station for docking the monitor 130. In one implementation, the external component is a box, such that the magnet 620 is coupled to a lid of the box that is used to store the heart monitoring device 130. As a subject opens the lid of the box, the magnet moves away from the heart monitoring device 130, disengaging the reed switch 610 which may be detected by the heart monitoring device 130. The reed switch 610 indicates when the monitor 130 is in the box, allowing for a particular computer program (e.g., on a smart phone or other electronic computing device) to operate for performing first-use setup of the monitor 130. Similarly, in the case of a base station, the reed switch 610 may report docked status, which may be used to operate various associated programs on a smart phone or other electronic computing device. In other embodiments, other sensors or switches different from a reed switch may be used to accomplish these mode-detection operations.

III.G.III. Inertial Measurement Units

The IMUs (also referred to herein as movement sensors) detect movement of the heart monitoring device 130. In one embodiment, the movement sensors detect up to three axes of translational movement. The movement sensors may include an accelerometer, which may be used to obtain acceleration, velocity, and position information. The movement sensors may also include a gyroscope capable of detecting three axes of rotational movement. The movement sensors may also include a magnetometer for measuring magnetic fields along three axes. Together, the movement sensors help to provide contextual information regarding a subject's movement of the heart monitoring device 130 during a recording of the subject's heart activity. The movement sensors can detect whether the heart monitoring device 130 is moving above a movement threshold which may also be reported as a movement artifact.

IV. Method for Accurately Measuring Heart Activity

A controller of the heart monitoring device 130 monitors and coordinates data capture between the various sensors of the heart monitoring device 130. In one embodiment, the controller has a circuit board 280 with the battery 260 providing power to the circuit board 280 with electronic lead 285, as shown in FIG. 2G. The controller signals when any of the electrodes 220, the pulse oximeters 230, the Doppler sensor 270, and the force sensor 275 begin to measure; the controller also stores and transmits data from the audio microphones 210, the electrodes 220, the pulse oximeters 230, the Doppler sensor 270, the force sensor 275, and the reed switch 610. The controller receives audio data from the audio microphones 210 including the acoustic signals recorded by each audio microphone 210. The controller receives confirmation from the pulse oximeters 230 that the subject's finger is keyed into the groove 240. The controller receives confirmation from the electrodes 220 that the two electrical circuits are completed. The controller receives confirmation from the second audio microphone 210 that the heart monitoring device 130 is pressed against the subject's chest. The controller may also receive confirmation from the force sensor 275 that the heart monitoring device 130 is sufficiently pressed against the subject's chest by comparing the pressure data from the force sensor 275 to a threshold pressure. The controller signals the electrodes 220, the pulse oximeters 230, and the Doppler sensor 270 to begin recording. The controller receives two sets of EKG data from the electrodes 220 corresponding to the two electrical circuits. The controller receives two sets of blood oxygen level data from each pulse oximeter 230. The controller also receives a set of Doppler shift signal data from the Doppler sensor 270. In other embodiments, the controller may additionally receive two sets of pressure data from two force sensors 275—a first force sensor 275 coupled to a chest electrode and a second force sensor 275 coupled to the thumb electrode. The controller transmits all data including the audio data, the two sets of heart electrical activity data, the two sets of blood oxygen level data, and the Doppler shift signal data to an external system through an established wireless connection.

Figure 7:
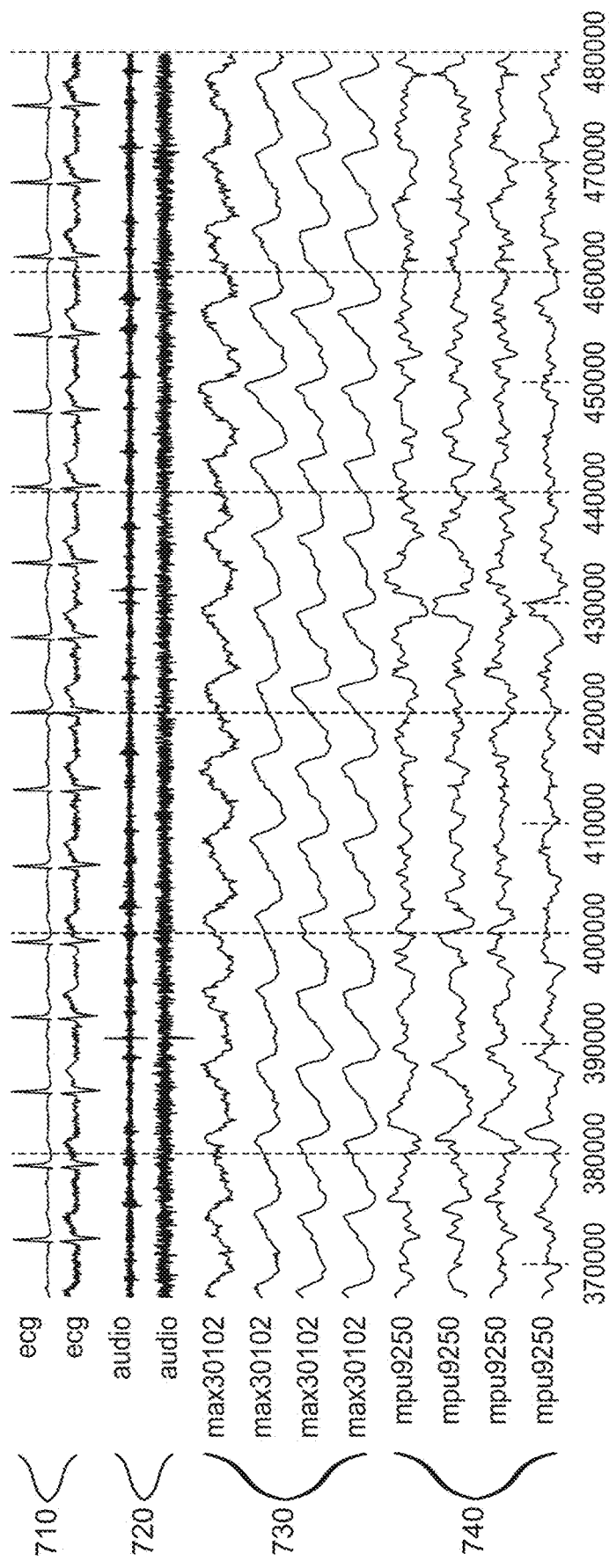
FIG. 7 illustrates a graph of recorded data by the heart monitoring device, according to an embodiment.

FIG. 7 is a graph over time of recorded data by the heart monitoring device 130, according to an embodiment. The recorded data by the heart monitoring device may have been recorded during a single recording session by the heart monitoring device. A recording session may be a period of time where one or more sensors of the heart monitoring device are activated to record heart data. In this embodiment, the heart monitoring device 130 contains the three electrodes 220 configured to record two sets of heart electrical activity data 710 with each set labeled "ecg" for the two electrical circuits completed by the three electrodes. The heart monitoring device 130 also has the two microphones 210 recording two sets of audio data 720 with each set labeled "audio". In this embodiment, the heart monitoring device 130 operates two pulse oximeters 230 to emit and receive light over two ranges of wavelengths resulting in four sets of pulse oximeter data 730 with each set labeled "max 30102". Additionally, the heart monitoring device 130 measures four sets of movement data from the movement sensors including three axes of translational movement and one axes of rotational movement with each set labeled "mpu9250".

Figure 8:
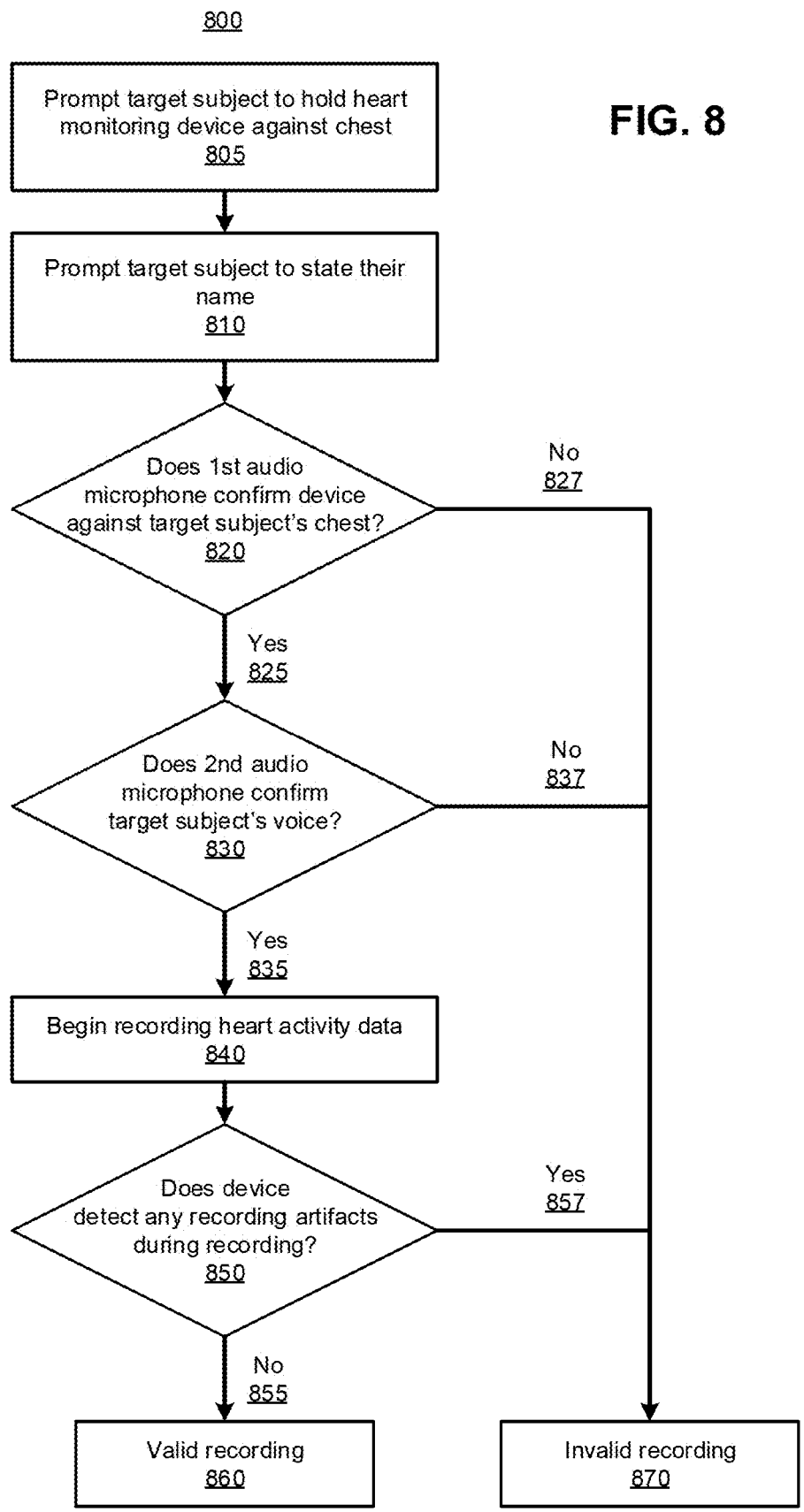
FIG. 8 illustrates a flowchart describing a method of accurately recording heart data of a target subject, according to an embodiment.

FIG. 8 illustrates a flowchart describing a method 800 of accurately recording heart data of a target subject, in accordance with an embodiment. The method 800 is implemented with the heart monitoring device 130 for accurately recording the target subject. In one embodiment, an insurance company (e.g., a medical insurance company or a life insurance company) may benefit from the use of this method 800 to avoid the target subject from cheating the recording of that target subject's heart data.

The method 800 begins with prompting 805 the target subject to hold the heart monitoring device 130 against the target subject's chest to begin recording heart data. The heart monitoring device 130 may prompt the target subject with audio instructions that may be presented through an audio speaker. Alternatively, the heart monitoring device 130 may prompt the target subject with instructions presented on an application on an external device (e.g., a mobile device) that is wirelessly connected to the heart monitoring device. In other embodiments, the heart monitoring device 130 may be accompanied with physical instructions. Once the heart monitoring device 130 is pressed against the target subject's chest, the electrodes and the audio microphone placed on the bottom surface of the heart monitoring device are in contact with the target subject's chest.

In some embodiments, the method 800 includes a step following the prompting 805 to determine whether the heart monitoring device 130 is firmly held against the chest. In these embodiments, the heart monitoring device 130 may use any combination of one or more of the sensors or components to determine whether the heart monitoring device 130 is firmly held against the chest. In one implementation, the heart monitoring device 130 uses the force sensor 275 coupled to the bottom surface of the heart monitoring device 130 to detect an amount of force applied by the chest on the force sensor or correspondingly the force applied to hold the heart monitoring device 130 on the chest. The determination of whether the heart monitoring device 130 is firmly held against the chest may be determined by the detected amount of force surpassing a threshold force. In another embodiment, the heart monitoring device 130 detects whether or not the electrodes 220 can complete a circuit between a right thumb electrode 132 and a chest electrode 136 or 138. If the electrodes 220 can complete a circuit, then the heart monitoring device 130 may also confirm that the same subject holding the heart monitoring device 130 with their right hand also is pressing the heart monitoring device 130 against their chest.

The method 800 continues with prompting 810 the target subject to verbally state the target subject's name. The prompting may be provided by audio instructions presented through an audio speaker or instructions presented by other means discussed in step 805. In alternate embodiments, the heart monitoring device may prompt 810 the target subject to verbally state another phrase or string of words, e.g., "the quick brown fox jumps over the lazy dog."

The method 800 makes a determination 820 whether an audio microphone 210 coupled to the bottom surface of the heart monitoring device 130 confirms that the heart monitoring device 130 is against the chest of the target subject. The audio microphone 210 coupled to the bottom surface of the heart monitoring device 130 records acoustic signals from the chest. The acoustic signals from the chest may originate from the target subject verbally speaking in response to the prompting 810 with acoustic waves resonating through the chest cavity. The acoustic signal detected by the audio microphone 210 corresponding to acoustic waves resonating through the chest cavity may be compared against a threshold acoustic signal to determine 820 whether the first audio microphone confirms that the heart monitoring device 130 is against the chest of the target subject. If the heart monitoring device 130 confirms 825 that the heart monitoring device is against the chest of the target subject using the acoustic signal from the audio microphone 210, then the heart monitoring device 130 may proceed with subsequent steps of the method 800. If the heart monitoring device 130 rejects 827 that the heart monitoring device 130 is against the chest of the target subject, the heart monitoring device 130 concludes an invalid recording 870. In one instance of a target subject attempting to cheat the recording, the target subject may verbally respond to the prompt 810; however, another subject may be holding the heart monitoring device 130 against their chest. In this scenario, the heart monitoring device 130 would detect an acoustic signal as insufficient of confirming 825 the heart monitoring device 130 is against the target subject's chest and would reject the recording as an invalid recording 870.

The method 800 also makes a determination 830 whether a second audio microphone coupled to another surface (i.e., not the bottom surface) of the heart monitoring device 130 confirms the target subject's voice. In the flowchart embodiment of FIG. 8, the step 830 follows step 820; in other embodiments, the two steps may occur simultaneously or in reverse order. Another audio microphone 210 detects an acoustic signal which can be used for speaker recognition or in some instances more specifically speaker verification. The heart monitoring device 130 uses speaker recognition to determine whether the detected acoustic signals match a ground truth acoustic signal of the target subject's voice. The ground truth acoustic signal may be received prior to the method 800. In some cases, the ground truth acoustic signal is a ground truth of the target subject's voice stating the prompted speech in step 810. For example, the heart monitoring device 130 received a recording of the target subject stating their name before the method 800. In examples where an insurance company may take advantage of the method 800, the insurance company may record the target subject's name through an in-person appointment or through a call. Following the example of the heart monitoring device 130 using a recording of the target subject stating their name, during the method 800, the heart monitoring device 130 compares the detected acoustic signal of the target subject stating their name after being prompted 810 with the ground truth acoustic signal of the target subject stating their name which was received prior to the method 800. In some embodiments, the heart monitoring device 130 may employ various voice recognition algorithms (e.g., frequency estimation models, hidden Markov models, Gaussian mixture models, pattern matching algorithms, machine learning algorithms, etc.) for determining 830 whether the second audio microphone verifies the target subject speaking.

If the heart monitoring device 130 confirms 835 that the target subject is speaking, the heart monitoring device 130 may proceed with a subsequent step of the method 800. If the heart monitoring device 130 rejects 837 the acoustic signal as not matching the target subject's ground truth acoustic signal, the heart monitoring device 130 may conclude an invalid recording 870. In a simple example, the heart monitoring device 130 may utilize speaker recognition to prevent a target subject from having another subject state the target subject's name while holding the heart monitoring device 130 to cheat the recording of the target subject's heart data. In some embodiments, the heart monitoring device 130 further implements a noise cancellation model to improve a signal to noise ratio of the detected acoustic signals. If the heart monitoring device 130 detects above a threshold amount of noise in the detected acoustic signal, the heart monitoring device 130 may reject 837 the detected acoustic signal and conclude an invalid recording 870. In one example, the noise cancellation model prevents a target subject from throwing off the speaker recognition process by attempting to evade the speaker recognition with an excess of noise whether by drowning out the target subject's voice or another's voice impersonating the target subject's voice.

In other embodiments, the heart monitoring device 130 may further compare the detected acoustic signals from the two audio microphones 210 for confirming a synchronicity in the detected acoustic signals. The heart monitoring device 130 compares the two sets of detected acoustic signals and determines whether the two audio microphones 210 recorded acoustic signals with synchronicity. The heart monitoring device 130 may compare various characteristics of each set of the detected acoustic signals, e.g., frequencies, time signatures, amplitudes, etc. In one example, the heart monitoring device 130 considers whether the time signatures of the acoustic signals match. If one set of acoustic signals is temporally offset from the other set of acoustic signals, then the heart monitoring device 130 may also conclude an invalid recording 870. In another example, the heart monitoring device 130 considers frequencies of the two sets of detected acoustic signals. If one set of acoustic signals has frequencies that differ above a threshold differential from the frequencies of the other set of acoustic signals, then the heart monitoring device 130 may also conclude an invalid recording.

Upon confirming the target subject is, in fact, the person holding the heart monitoring device 130 properly against the target subject's chest, the method 800 proceeds with recording 840 heart data of the target subject. In the embodiment of the flowchart, the method 800 proceeds with recording 840 heart data after confirming 825 that the heart monitoring device 130 is properly against the chest and confirming 835 that the target subject is holding the heart monitoring device 130. The heart monitoring device 130 records heart data 840 with the electrodes 220 and the other various sensors on the heart monitoring device 130. The heart monitoring device 130 records heart EKG data of the target subject with the electrodes 220 which is accomplished with the principles discussed in Section III.D. EKG Monitoring. The heart monitoring device 130 may additionally record any combination of audio data from the audio microphones 210, blood oxygen level data from pulse oximeters 220 which can record, force data from the force sensor 275 describing a force applied to hold the heart monitoring device 130 against the target subject's chest, Doppler data from the Doppler sensor 270 which can be used to determine blood flow rate, movement data from a plurality of movements sensors (e.g., accelerometers, gyroscopes, etc.) which can determine record movement up to six degrees of freedom (i.e., three translation degrees of freedom and three rotational degrees of freedom). The heart monitoring device 130 may store all the recorded heart data in a storage medium of the controller.

The method 800 follows with determining 850 whether the heart monitoring device 130 detects any recording artifacts during the recording of the heart data. The heart monitoring device 130 may determine a recording artifact with any of the sensors or components. A recording artifact may be either a movement artifact where the heart monitoring device 130 detects a suspect movement of the heart monitoring device 130 or a circumstantial artifact where the heart monitoring device 130 detects a suspect circumstance in the environment when recording. The heart monitoring device 130 may also tag each recording artifact with a time of occurrence.

In one embodiment, the heart monitoring device 130 uses the electrodes to detect substantial movement of the heart monitoring device 130 away from the target subject's chest. The heart monitoring device 130 may calculate a noise signal from the EKG data recorded by the electrodes during the recording session. The noise signal is dependent on a good contact between the electrodes and the target subject's chest. The heart monitoring device 130 may compare the noise signal to a threshold noise signal. If the noise signal surpasses the threshold, the heart monitoring device 130 may determine instances that the noise signal surpasses the threshold as movement artifacts during the recording session. If the noise signal remains below the threshold, the heart monitoring device 130 may determine no movement artifacts at least based on the EKG data.

In one embodiment, the heart monitoring device 130 uses the movement sensors to detect substantial movement up to six degrees of freedom which can be deemed a movement artifact. If the heart monitoring device 130 detects any movement in any of the six degrees of freedom above a threshold movement, the heart monitoring device 130 may determine that movement to be a movement artifact.

In one embodiment, the heart monitoring device 130 uses the force sensor 275 to detect a decrease in contact between the heart monitoring device 130 and the target subject's chest. If the force sensor records a decrease in force applied by the target subject's chest on the force sensor 275, the heart monitoring device 130 may determine whether the force applied is below a threshold force to be considered properly held against the chest, the heart monitoring device 130 may determine that instance to be a movement artifact.

In one embodiment, the heart monitoring device 130 may use the audio microphones 210 to detect any sounds that may interfere with accurately recording the target subject's heart data. In one example, the heart monitoring device 130 determines a sharp, loud, and startling sound detected by an audio microphone to be a circumstantial artifact which can affect the recording of the heart data.

In other embodiments, other sensors may be used to detect whether other circumstances (e.g., temperature, humidity, etc.) are circumstantial artifacts that may affect the recording of the heart data. The heart monitoring device 130 assesses whether or not recording artifacts were detected during the recording. If the heart monitoring device 130 determines 857 there were any recording artifacts, then heart monitoring device 130 may conclude an invalid recording 870. If the heart monitoring device 130 determines 855 there were not any recording artifacts, the heart monitoring device 130 may conclude that the method 800 achieved a valid recording 860. The valid recording 860 may include all the recorded heart data from the heart monitoring device.

If the method 800 achieves a valid recording 860, the heart monitoring device 130 may transmit the valid recording 860 to an external device or server. In implementations by the insurance companies, the heart monitoring device 130 may transmit the valid recording 860 to the insurance companies. In other embodiments, the heart monitoring device 130, another device, or the server can score the valid recording 860. The score may then be transmitted to the insurance companies, solely or with the recorded heart data.

If the method 800 achieves an invalid recording 870 at any stage of the method 800, the heart monitoring device 130 may repeat the method 800 until a valid recording 860 is achieved. In some embodiments, the heart monitoring device 130 may repeat one or more steps prior in the method 800 from the step that lead to the conclusion of an invalid recording 870. In one example, if the heart monitoring device 130 determines at 820 to reject 827, via the first audio microphone, that the heart monitoring device 130 is not properly held against the chest, then the heart monitoring device 130 may repeat step 805 for prompting the target subject to hold the heart monitoring device 130 against their chest and/or step 810 for prompting the target subject to state their name. In another example, if the heart monitoring device 130 determines at 830 to reject 837, via the second audio microphone, that the target subject has not been properly verified to be holding the heart monitoring device 130, then the heart monitoring device 130 may repeat step 810 for prompting the target subject to state their name. In yet another example, if the heart monitoring device 130 determines at 850 there has been detected 857 any recording artifacts, then the heart monitoring device 130 may repeat the recording 840 step and/or the entire method 800 including the confirmations of step 820 and step 830, potentially based on a severity of the recording artifact. For example, the heart monitoring device 130 may determine to repeat the recording 840 of the heart data if the recording artifact detected at 857 was a circumstantial artifact such as a startling sound; whereas, if the recording artifact detected at 857 was a movement artifact, then the heart monitoring device 130 may repeat the verification process as well.

V. Additional Configurations

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

Some portions of this description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the patent rights. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights, which is set forth in the following claims.

What is claimed is:

1. A heart monitoring device comprising:
an enclosure sized to fit a subject's right hand with a top surface for coupling to the subject's right hand and a bottom surface for coupling to the subject's chest, the enclosure comprising:
a first groove on the top surface and sized to fit a corresponding phalange of the subject's right hand, wherein the heart monitoring device has a proper orientation for recording heart activity of the subject, the proper orientation comprising a range of orientations of the heart monitoring device relative to the subject when the heart monitoring device is held by the subject with the corresponding phalange keyed into the first groove;
a plurality of electrodes placed on the enclosure and configured to create one or more electrical circuits across a human heart when the heart monitoring device is in the proper orientation, the plurality of electrodes including;
a first electrode placed on a surface of the enclosure for coupling to a portion of the subject's right hand, and
a second electrode and a third electrode placed on the bottom surface of the enclosure for coupling to the subject's chest; and
a plurality of pulse oximeters placed in the first groove and configured to measure blood oxygen levels of the corresponding phalange when the corresponding phalange is keyed into the first groove.

2. The heart monitoring device of claim 1, wherein the enclosure comprises:
a second groove on the side surface of the enclosure and sized to fit a subject's right thumb,
wherein the first electrode is a right thumb electrode that is placed in the second groove.

3. The heart monitoring device of claim 1, wherein at least some of the plurality of electrodes are dry contact electrodes comprising a conductive surface with topographical features, the conductive surface for coupling to the subject.

4. The heart monitoring device of claim 3, wherein the conductive surface of each electrode is constructed with silver.

5. The heart monitoring device of claim 1, wherein the electrical circuits created by the plurality of electrodes includes:
a first electrical circuit that is completed with the first electrode and the second electrode which is used by the heart monitoring device to define a first lead across the subject's heart; and
a second electrical circuit that is completed with the first electrode and the third electrode which is used by the heart monitoring device to define a second lead across the subject's heart.

6. The heart monitoring device of claim 5, wherein the first lead and the second lead are noncollinear based at least in part on the proper orientation of the heart monitoring device relative to the subject.

7. The heart monitoring device of claim 6, wherein a third lead is calculated based at least in part on a basis formed by the first lead and the second lead.

8. The heart monitoring device of claim 1, further comprising:
a first audio microphone placed within the enclosure and configured to record acoustic signals from a local area of the heart monitoring device.

9. The heart monitoring device of claim 8, further comprising:

a second audio microphone placed within the enclosure in proximity to the bottom surface of the enclosure and configured to record acoustic signals from the subject's chest.

10. The heart monitoring device of claim 9, further comprising:
a Doppler sensor placed on the bottom surface of the enclosure and configured to record a Doppler shift signal corresponding to flow of blood in the subject.

11. The heart monitoring device of claim 1, further comprising:
a force sensor placed within the enclosure and coupled to one of the second electrode and the third electrode, wherein the force sensor is configured to measure a force applied onto the electrode to which the force sensor is coupled.

12. The heart monitoring device of claim 1, further comprising:
a movement sensor placed within the enclosure and configured to measure movement of the heart monitoring device.

13. A method for accurately recording heart activity of a target subject with a heart monitoring device, the method comprising:
prompting the target subject to hold the heart monitoring device in a proper orientation, wherein the proper orientation occurs when the subject's right hand holds the heart monitoring device against the subject's chest, such that a corresponding phalange on the subject's right hand keys into a first groove on a top surface of an enclosure of the heart monitoring device;
prompting the target subject to state a phrase while holding the heart monitoring device;
receiving a first acoustic signal from a first audio microphone placed within the enclosure in proximity to a bottom surface of the enclosure and configured to record acoustic signals from the subject's chest;
determining whether the target subject is holding the heart monitoring device against the target subject's chest based at least in part on the first acoustic signal;
activating one or more sensors of the heart monitoring device to measure heart data;
receiving the heart data from the sensors from a recording session;
determining presence of or lack of one or more recording artifacts during the recording session based at least in part on the heart data; and
responsive to determining a lack of recording artifacts during the recording session, determining the recording session to be a valid recording.

14. The method of claim 13, wherein the determining whether the target subject is holding the heart monitoring device against the target subject's chest based at least in part on the first acoustic signal comprises:
determining that the first acoustic signal is above a threshold intensity,
wherein the determining whether the target subject is holding the heart monitoring device against the target subject's chest is based on the determining that the first acoustic signal is above a threshold intensity.

15. The method of claim 13, further comprising:
receiving a second acoustic signal from a second audio microphone placed within the enclosure in proximity to the top surface of the enclosure and configured to record acoustic signals from a local area of the heart monitoring device.

16. The method of claim 15, wherein the determining whether the target subject is holding the heart monitoring device against the target subject's chest is also based at least in part on the second acoustic signal comprises:
determining that the second acoustic signal matches a ground truth acoustic signal of the target subject's voice.

17. The method of claim 15, wherein the determining whether the target subject is holding the heart monitoring device against the target subject's chest is based at least in part on the first acoustic signal and the second acoustic signal comprises:
determining a synchronicity between the first acoustic signal and the second acoustic signal,
wherein the determining whether the target subject is holding the heart monitoring device against the target subject's chest is also based on the synchronicity.

18. The method of claim 13, wherein the sensors include a plurality of electrodes completing one or more electrical circuits across the target subject's heart, and wherein the heart data comprises EKG data including one or more leads measured by the plurality of electrodes with the completed electrical circuits.

19. The method of claim 18, wherein the determining presence of or lack of one or more recording artifacts during the recording session based at least in part on the heart data comprises:
calculating a noise signal from the EKG data; and
determining whether the noise signal surpasses a threshold noise signal,
wherein the determination that the noise signal surpasses the threshold noise signal corresponds to determining a presence of one or more recording artifacts, and
wherein the determination that the noise signal is below the threshold noise signal corresponds to determining a lack of one or more recording artifacts.

20. A system comprising:
a processor; and
a non-transitory computer-readable storage medium with encoded instructions that, when executed by the processor, cause the processor to accomplish steps of:
prompting a target subject to hold a heart monitoring device in a proper orientation, wherein the proper orientation occurs when the subject's right hand holds the heart monitoring device against the subject's chest, such that a corresponding phalange on the subject's right hand keys into a first groove on a top surface of an enclosure of the heart monitoring device;
prompting the target subject to state a phrase while holding the heart monitoring device;
receiving a first acoustic signal from a first audio microphone placed within the enclosure in proximity to a bottom surface of the enclosure and configured to record acoustic signals from the subject's chest;
determining whether the target subject is holding the heart monitoring device against the target subject's chest based at least in part on the first acoustic signal;
activating one or more sensors of the heart monitoring device to measure heart data;
receiving the heart data from the sensors from a recording session;
determining presence of or lack of one or more recording artifacts during the recording session based at least in part on the heart data; and responsive to determining a lack of recording artifacts during the recording session, determining the recording session to be a valid recording.

21. A heart monitoring device comprising:
   an enclosure sized to fit a subject's hand with a top surface for coupling to the subject's hand and a bottom surface for coupling to the subject's chest;
   a plurality of electrodes placed on the enclosure and configured to create one or more electrical circuits across a human heart when the heart monitoring device is held in the subject's hand against the subject's chest, the plurality of electrodes including:
      a first electrode placed on a surface of the enclosure for coupling to a portion of the subject's right hand, and
      one or more chest electrodes placed on the bottom surface of the enclosure for coupling to the subject's chest.

* * * * *